US006274724B1

(12) United States Patent
Rasmussen et al.

(10) Patent No.: US 6,274,724 B1
(45) Date of Patent: Aug. 14, 2001

(54) CYCLIC IMIDAZOLE COMPOUNDS HAVING RELATIVELY LOW HYDROGEN CONTENT AND RELATIVELY HIGH NITROGEN CONTENT AND POLYMERS AND COPOLYMERS FORMED THEREFROM

(75) Inventors: Paul G. Rasmussen, Ann Arbor; Sarah E. Reybuck, St. Joseph; David M. Johnson; Richard G. Lawton, both of Ann Arbor, all of MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/329,618

(22) Filed: Jun. 10, 1999

Related U.S. Application Data

(62) Division of application No. 09/059,800, filed on Apr. 14, 1998, now Pat. No. 6,096,899.

(51) Int. Cl.$^7$ .......................... G07H 21/02; G07H 21/04; G07H 21/00
(52) U.S. Cl. ................. 536/25.3; 536/25.31; 536/25.33; 536/25.34
(58) Field of Search ............................. 536/25.3, 25.31, 536/25.33, 25.34

(56) References Cited

U.S. PATENT DOCUMENTS

| | | |
|---|---|---|
| 2,534,331 | 12/1950 | Woodward . |
| 3,778,446 | 12/1973 | Weigert . |
| 3,806,517 | 4/1974 | Begland . |
| 4,097,475 | 6/1978 | James . |
| 4,220,466 | 9/1980 | Patel . |
| 4,299,939 | 11/1981 | Panzer . |
| 4,410,706 | 10/1983 | Rothenberg . |
| 4,417,046 * | 11/1983 | Hsiung .................................. 536/27 |
| 4,585,724 | 4/1986 | Helling . |
| 4,600,681 | 7/1986 | Bergthaller . |
| 5,021,540 | 6/1991 | Leone-Bay . |
| 5,122,563 | 6/1992 | Kaminski . |
| 5,523,008 | 6/1996 | Boden . |
| 5,663,126 | 9/1996 | Boden . |
| 5,674,436 | 10/1997 | Breitenbach . |
| 5,677,384 | 10/1997 | Detering . |
| 5,712,408 | 1/1998 | Rasmussen . |
| 5,856,464 * | 1/1999 | Livingston ........................... 536/25.3 |
| 5,965,721 * | 10/1999 | Cook et al. ........................... 536/23.1 |
| 6,028,188 * | 2/2000 | Arnold et al. ....................... 536/25.3 |
| 6,031,092 * | 2/2000 | Just et al. ........................... 536/25.34 |
| 6,051,699 * | 4/2000 | Ravikumar ........................... 536/25.3 |

FOREIGN PATENT DOCUMENTS

| | | |
|---|---|---|
| 44 29 464 | 2/1996 | (DE) . |
| 49-134676 | 12/1974 | (JP) . |
| WO 97/14706 | 4/1997 | (WO) . |
| WO 97/14710 | 4/1997 | (WO) . |

OTHER PUBLICATIONS

P.S. Robertson and J. Vaughan, "Derivatives of the Hydrogen Cyanide Tetramer: Structure and Chemistry," (Dept. of Chemistry, University of Canterbury), Jun. 5, 1958, 2691–2693.

Yoshitaka Yamada, Izumi Kumashiro and Tadao Takenishi, "Synthesis of 4,5–Di– and 1,4,5–Trisubstituted Imidazole Derivatives from 4,5–Dicyanoimidazole," Bulletin of the Chemical Society of Japan, vol. 41, 1237–1240 (1968).

D.S. Donald and O.W. Webster, "Synthesis of Heterocycles from Hydrogen Cyanide Derivatives," Advances in Hererocyclic Chemistry, vol. 41, 6–9 (1987).

Herman F. Mark, Norbert M. Bikales, Charles G. Overberger, Georg Menges, and Jacqueline I. Kroschwitz, Encyclopedia of Polymer Science and Engineering, vol. 12, "Polyesters to Polypeptide Synthesis," 346–347 (1988).

David S. Allan, Ernest L. Thurber and Paul G. Rasmussen, "Polymers Containing Cyanoimidazole Pendant Groups", Journal of Polymer Science: Part A: Polymer Chemistry, vol. 28, 2475–2483 (1990).

PCT Search Report, Nov. 25, 1997, PCT/US97/14039 (Aug. 8, 1997).

Chemical Abstracts, vol. 82, No. 25, Jun. 23, 1975, Columbus, Ohio, US, Abstract No. 170924q.

Chemical Abstracts, vol. 83, No. 24, Dec. 15, 1975, Columbus, Ohio, US, Abstract No. 195237B; and.

Chemical Abstracts, vol. 126, No. 20, May 19, 1997, Columbus, Ohio, US, Abstract No. 264400v.

Marvin H. Caruthers, "Gene Synthesis Machines: DNA Chemistry and Its Uses," Journal of Chemical Education, vol. 230, Oct. 1985, 281–285.

Marvin H. Caruthers, "Chemical Synthesis of DNA," Concepts in Chemistry, Journal of Chemical Education, vol. 66, No. 7, Jul. 1989, 577–580.

M.D. Matteucci and M.H. Caruthers, "The Synthesis of Oligodeoxypyrimidines on a Polymer Support," Tetrahedron Letters, vol. 21, pp 719–722, Pergamon Press Ltd, Great Britain (1980).

Robert L. Letsinger and V. Mahadevan, "Stepwise Synthesis of Oligodeoxyribonucleotides on an Insoluble Polymer Support," Journal of the American Chemical Society, 88:22, Nov. 20, 1966, pp 5319–5324.

Theophyl Eicher and Dieter Lerch, "Zur Reaktionsweise Des 3–Ethoxy–1,2–Diphenyl–Cyclopropenyliukations Mit Bifunktionellen Aromatischen Aminen," *Tetrahedron Letters*, vol. 21, pp 3751–3754 (1980).

* cited by examiner

Primary Examiner—Floyd D. Higel
(74) Attorney, Agent, or Firm—Harness, Dickey & Pierce, P.L.C.

(57) ABSTRACT

In one embodiment, the invention provides a polymer comprising imidazole ring units having nitrogen at the 1 and 3 positions of the ring; a carbon at each of the 2, 4 and 5 positions of the ring; and radical substituents G1 and G2 carried at the 4 and 5 positions. G1 and G2 are each independently selected from cyano, substituents derived from cyano, and substituents which replace cyano. The polymers formed by at least two of the cyclic imidazole units. In another embodiment, the invention provides new imidazole compounds usable as monomers to form the polymers. In still another embodiment, the invention provides a method for using the polymers as a coupling/activator for synthon synthesis.

10 Claims, 15 Drawing Sheets

ACRODAMN → VINAZENE

METHYL VINAZENE

| Polymer soln. conc. (g/cm^3) | Relative Viscosity | Inherent Viscosity | Specific Viscosity | Reduced Viscosity |
|---|---|---|---|---|
| 0.0150 | 2.242 | 53.825 | 1.2420 | 82.80 |
| 0.0125 | 2.001 | 55.492 | 1.0010 | 80.08 |
| 0.0107 | 1.818 | 55.789 | 0.8180 | 76.35 |
| 0.0094 | 1.690 | 55.971 | 0.6900 | 73.60 |

CYCLIC IMIDAZOLE COMPOUNDS HAVING RELATIVELY LOW HYDROGEN CONTENT AND RELATIVELY HIGH NITROGEN CONTENT AND POLYMERS AND COPOLYMERS FORMED THEREFROM

CROSS REFERENCE TO RELATED APPLICATIONS

This application is a divisional of U.S. application Ser. No. 09/059,800, filed Apr. 14, 1998, now U.S. Pat. No. 6,096,899.

FIELD OF THE INVENTION

The present invention relates to compounds and polymers based on and formed from imidazoles and methods for preparing same.

BACKGROUND OF THE INVENTION

Heterocyclic compounds are commonly used in industry. Imidazoles are monocyclic heteroatomic ring compounds. Derivatives of imidazoles are used for dewatering of aqueous suspensions of organic and inorganic materials in waste water treatment. They are used for diverse purposes such as agricultural chemicals, insecticides, and catalysts. The Encyclopedia of Polymer Science and Engineering, Vol. 12 (1988) reports that it is very difficult to synthesize imidazole monomers. Imidazole polymers can also be very difficult to synthesize. For this reason, imidazole compounds and polymers are used in limited quantities and are very costly.

Presently, there is a need for new polymers having heterocyclic monomer units which provide properties derived from their relatively low hydrogen content and relatively high nitrogen content. For example, polymers formed from heterocyclic compounds are expected to provide a number of useful characteristics including flame resistance. Other important uses are anticipated if such polymers are able to be synthesized cost-effectively.

SUMMARY OF THE INVENTION

It is an object of the present invention to provide a new family of cyclic imidazole ring compounds which are generally based on new 2-vinyl-4,5-dicyanoimidazoles. Another object is to provide polymers and copolymers formed from such compounds. Another object is to provide methods of synthesis which permit production of the new compounds and polymers from relatively inexpensive precursors, and which are suitable for scale-up to commercial processing. Still another object is to provide methods for using the new compounds and polymers of the invention. In particular, another object is to provide a method for using the new polymers in oligonucleotide synthesis.

The invention provides new compounds having a cyclic imidazole ring structure with specialized functional groups carried on the ring. Such groups are included prior to polymerization or after. In one embodiment, a given group is included prior to polymerization, then removed, and replaced by another group after polymerization.

In one embodiment, the cyclic compound of the invention has the formula as per FIG. 1, where R1 is characterized by being hydrogen or organic substituent that does not interfere with polymerization, and by being attachable to the cyclic compound by an electrophilic agent. It is preferred that the cyclic compound have the formula as shown in FIG. 1, where R1 represents an organic group, or hydrogen, and is preferably an organic group having one or more carbon atoms. Most preferably, R1 is a substituted or unsubstituted alkyl having 1 to 10 carbon atoms. Preferably, R1 is selected from the group consisting of methyl, ethyl, propyl, isobutyl, benzyl, nonyl, and carbamoyl. In a variation on the embodiment shown in FIG. 1, the substituent carried at the 1-nitrogen position may be more generally represented as E, which is any substituent, and preferably is attachable to the nitrogen by an electrophilic agent, and is not necessarily hydrogen or organic.

Referring to FIG. 2, the cyclic compound has the formula as shown where R1, R2 and R3 are identical or different and are each independently selected from the group consisting of hydrogen and organic substituents having 1 to 10 carbon atoms. It is preferred that at least of R1 and R2 is selected from the class of organic substituents where such substituents do not interfere with polymerization. It is preferred that R1 be any group attachable to the cyclic compound by an electrophilic agent. As in the case earlier described with respect to FIG. 1, R1 may be a substituent such as hydrogen or an organic substituent, with R1 being E as per above.

In one preferred embodiment, R1 and R2 are each hydrogen or substituted or unsubstituted alkyls, with R2 having 1 to 4 carbon atoms and R1 having 1 to 10 carbon atoms. It is necessary that the substituent, whether hydrogen, organic (R), or more broadly E, is sterically non-hindering. In the most preferred embodiment, R3 is hydrogen and R2 is selected from the group of methyl, ethyl, propyl and butyl.

Polymers formed by monomeric units of the invention are the polymers exemplified in FIGS. 3, 3A, 4, 4A, 9 and 10. The polymer generally comprises cyclic imidazole units having nitrogen at the 1 and 3 positions; a carbon at each of the 2, 4 and 5 positions; and radical substituents G1 and G2 carried at respective 4 and 5 positions. In one embodiment, G1 and G2 are each independently selected from cyano, substituents derived from cyano, and substituents which replace cyano. Polymers of the invention are formed by at least two of the cyclic imidazole units joined by linkage through any combination of linking carbon six and carbon seven carried on the ring at the 2 position carbon. Such linking carbons 6 and 7 are derived from vinyl carried at said 2 position carbon. In one embodiment the cyclic imidazole units are connected to a main polymer chain through linkage at the 2 position providing a polymer as exemplified in FIGS. 4, 4A, and 10.

In another embodiment, the polymer units are connected to one another by linkage through both the 1 and 7 positions. This is referred to in the art as "in chain linkage" or "ring in chain polymer". This is exemplified by FIGS. 3, 3A and 9.

The polymer of the invention provides surprising flexibility for substituents at the 1-nitrogen and 4,5 positions on the ring. This is exemplified in FIGS. 3A and 4A. Referring to FIGS. 3A and 4A, G1 and G2 are each independently selected from cyano, derivatives of cyano, and substituents which replace cyano on an imidazole ring. Examples include cyano, carboxy, carbamoyl, amide, amine, carboxylic acid and carboxylic ester. Broadly, E is essentially any substituent, and desirably E is attachable to the nitrogen by an electrophilic agent. Advantageously, E may serve a variety of functional uses such as provide fluorescence in an assay, or facilitate crosslinking. Examples of substituents carried at the E position include hydrogen, organic group, organic group having up to 10 carbon atoms, a catalytic substituent, a fluorescent substituent, a hydrophobic modifier substituent, a hydrophilic modifier substituent, and a crosslinking substituent.

The compounds and polymers of the invention are useful in a variety of applications, including synthesis of oligonucleotides. It is particularly preferred to use a vinylic polymer of the invention as exemplified in FIGS. 4, 4A and 10 for facilitating chemical synthesis of oligonucleotides. For this purpose, it is preferred to use the polymer exemplified in the figures, with R1 being hydrogen, namely, poly[1-(1H-4,5-dicyano-2-imidazoyl)ethylene]. To promote the coupling reaction used in laboratory synthesis of oligomers. In a typical synthesis method which exemplifies utility of the present polymer, deprotected nucleotide reacts with a protected monomer unit in a reaction mixture in the presence of a coupling agent. This forms a product of the reaction which is a 5'-protected oligonucleotide having its length increased by joining the monomer unit to the oligonucleotide. The desired product is separated from other reagents and unreacted substituents.

In accordance with the invention, the coupling agent is the polymer of the invention comprising cyclic imidazole units having nitrogen at the 1 and 3 positions; a carbon at each of the 2, 4 and 5 positions; and substituents G1 and G2 carried at respective 4 and 5 positions, where G1 and G2 are as defined earlier. It is preferred that each of G1 and G2 be an electron-withdrawing group, but need not necessarily be the same electron-withdrawing group. It is preferred that G1 and G2 are each independently selected from a group consisting of cyano, substituents derived from cyano, and substituents which replace cyano. It is most preferred that G1 and G2 each be cyano. As shown in FIG. 10, the polymer comprises imidazole units connected to the main polymer chain through the 2 position. It is preferred that R1 be hydrogen also, as shown in FIG. 10. With reference to FIG. 10 for convenience of illustration, the designation "IM" is used to represent alternate units of the 1H-4,5-dicyanoimidazole monomer unit.

The invention provides new compounds and polymers based on such compounds. The polymers are formed from monomeric units which were heretofore unavailable. Advantageously, the specific monomers of the invention are polymerizable by cost-effective methods to provide polymers having highly desirable properties. The invention advantageously provides new coupling agent (activator) for promoting phosphoramidite coupling reaction used in laboratory synthesis of oligomers. The invention advantageously provides relatively straight-forward and low-cost monomers, polymers, and synthesis methods which result in relatively good yields of desirable compounds, all readily adaptable to scale-up for commercial processing.

These and other objects, features, and advantages will become apparent from the following description of the preferred embodiments, claims, and accompanying drawings.

DETAILED DESCRIPTION OF THE PREFERRED EMBODIMENTS

Figure 1:
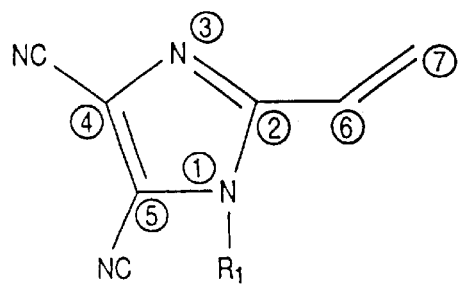
FIG. 1 is an illustration of a cyclic 2-vinyl imidazole compound.

The invention provides a new class of cyclic imidazole ring compounds which are generically based on new 2-vinyl-4,5-dicyanoimidazoles. The new compounds are usable as monomers to form polymers and copolymers. Specialized functional groups are carried on the ring. Such groups are included prior to polymerization or after. In another embodiment, a given group may be included prior to polymerization, then removed and replaced by another group after polymerization. The cyclic imidazole ring compounds have a formula as shown in FIG. 1. Preferably R1 is hydrogen if the polymerization is to be by thermalization. In the case of free radical polymerization, R1 may be hydrogen or an organic substituent that does not interfere with polymerization. In the case of anionic polymerization, R1 is an organic substituent that does not contain an acidic proton and does not interfere with polymerization. In another aspect, R1 is an organic substituent attachable to the cyclic ring structure by an electrophilic agent. It is preferred that R1 is a substituted or unsubstituted alkyl having 1–10 carbon atoms. It is desirable that R1 is an organic group having 1–10 carbon atoms. It is most preferred that R1 is selected from the group consisting of methyl, ethyl, propyl, isobutyl, benzyl, nonyl, and carbamoyl.

Figure 2:
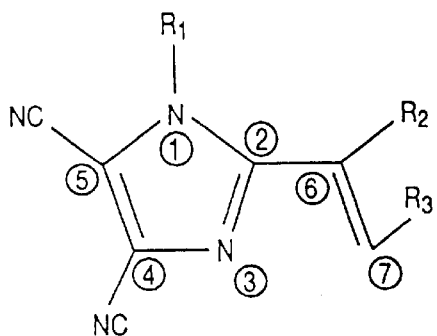
FIG. 2 is an illustration of another embodiment of a cyclic 2-vinyl imidazole compound.

In one embodiment, the cyclic compound has the formula as shown in FIG. 2, where R1, R2 and R3 are identical or different, and are each independently selected from the group consisting of hydrogen and organic radicals; provided that at least one of said R1 and R2 is selected from the organic substituents. The selection of substituents is limited to those that do not interfere with polymerization. The proviso that such substituents do not interfere with polymerization is understood in the art as exemplified by U.S. Pat. No. 5,138,007. It is desirable that R1 is any group attachable to the cyclic compound by an electrophilic agent. It is desirable that R1 is selected from the aforesaid groups described earlier. In one embodiment, R1 and R2 are each substituted or unsubstituted alkyls, with R2 having 1–4 carbon atoms, and R1 having 1–10 carbon atoms. The aforesaid selection criteria for the organic substituent requires that it be sterically nonhindering, so that the organic substituent is sterically nonhindering upon polymerization. It is preferred that R3 be hydrogen. It is preferred that R2 be selected from the group of methyl, ethyl, propyl, butyl and other simple alkyls. It should be noted that the terms "organic radical", "organic group", and "organic substituent", are used herein interchangeably.

In another aspect, the invention provides a polymer comprising cyclic imidazole units having nitrogen at the "1" and "3" positions; a carbon at each of the "2", "4", and "5" positions; where at least two of the cyclic imidazole units are connected to one another by linkage between any combination of: carbon at the 7 position, and nitrogen at the 1 position; or at least two of the cyclic imidazole units are joined to form a polymer by linkage between any combination of the aforesaid carbon at the 7 position and carbon at the 6 position. It is preferred that the polymer further comprise cyano groups carried at the respective 4 and 5 positions of the ring units. Aside from cyano groups, radical groups G1 and G2 may be carried at respective 4 and 5 positions, where G1 and G2 are each independently selected from the group consisting of cyano, substituents derived from cyano, and substituents which replace cyano. Preferably, G1 and G2 are each independently selected from cyano, carboxy, carbamoyl, and derivatives of cyanos, such as amides, amino, and carboxylic acids and carboxylic acid esters.

In one embodiment, G1 and G2 are, in the first instance, cyano groups which are carried into the reaction by DAMN or a DAMN derivative. Cyano groups are quite strongly electron withdrawing, and influence the properties of the imidazole. However, cyano groups also offer reactivity by which they can be readily converted to other groups. Thus, by action of acid or base, they may be hydrolyzed singly or together, to afford amide groups, carboxylic acid groups, or by alcoholysis, carboxylic ester groups. These groups are all somewhat electron withdrawing to the imidazole ring. Cyano groups also permit modification by Hoffman type reaction to afford electron-donating amine groups. Examples of conversion of cyano groups on imidazoles to other functional groups are known.

Figure 4:
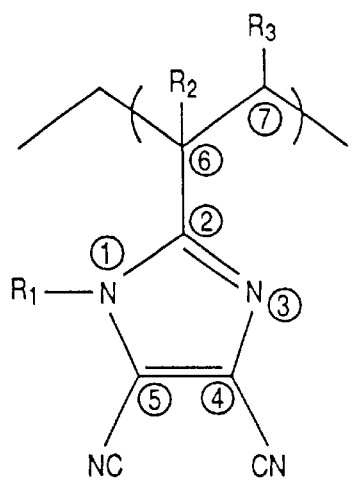
FIG. 4 is an illustration of a poly-imidazole, with the cyclic imidazole monomers joined to a main polymer chain by linkage at the 2 position carbon forming a poly [1-(2-imidazolyl)ethylene].
Figure 3:
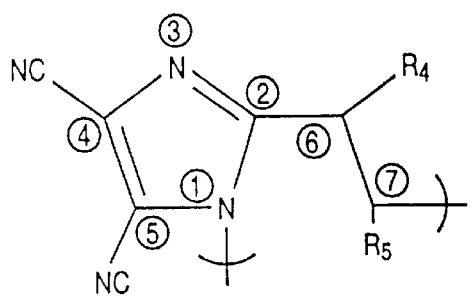
FIG. 3 is an illustration of a poly-imidazole, with the cyclic imidazole monomers joined to a main polymer chain by linkage at the 7 position carbon and 1 position nitrogen, forming an "in-chain" polyimidazole.
Figure 3A:
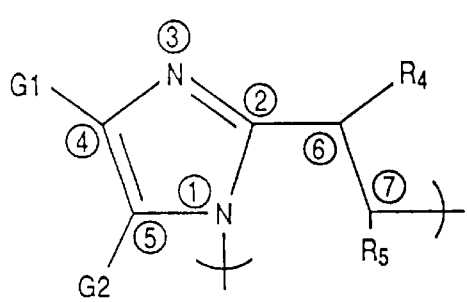
FIG. 3A is similar to FIG. 3, but the cyano groups at the 4 and 5 positions have been replaced by generic functional groups, independently selected G1 and G2.
Figure 4A:
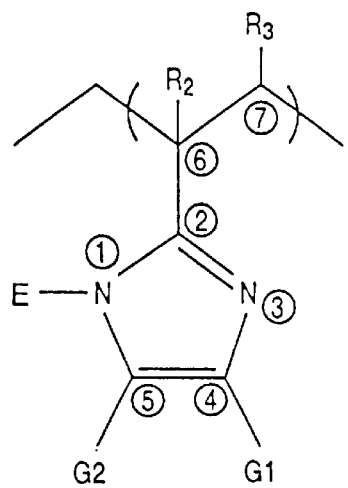
FIG. 4A is similar to FIG. 4, but the cyano groups at the 4 and 5 positions have been replaced by generic functional groups, independently selected G1 and G2; and generic group E replaces R1 at the 1 position nitrogen.

A polymer comprising repeat units of a monomer of the invention is exemplified by the formula of FIG. 3, where R4 and R5 are each independently selected from the group consisting of hydrogen and substituted or unsubstituted alkyls having 1–4 carbon atoms. In the case where each of R4 and R5 are alkyl, this is poly[(1-R4 alkyl-2-R5 alkyl) ethylene N(4,5 dicyano-2-imidazolyl)]. Another embodiment is shown by the polymer of FIG. 4, where R1, R2, and R3 are defined as immediately above. In the case where R1, R2 and R3 are each alkyl, this is poly[(1-(N-R1 alkyl-4,5-dicyano-2-imidazolyl)-1-R2 -alkyl-2-R3 alkyl ethylene]. Referring to FIG. 3(A), groups G1 and G2 may be cyano groups, or groups which replace the cyano groups. In another embodiment shown in FIG. 4(A), substituent group E replaces the R1. Preferably, E is a functional group attachable to the 1 position nitrogen by an electrophilic agent. In one embodiment, E is a catalytically active group which renders the polymer useful as a catalytic agent. In another embodiment, E may be a fluorescent group, where the polymer might be used for assay purposes. In still another embodiment, E may be a hydrophobic modifier. In still another embodiment, E may be a crosslinking agent that is a bifunctional electrophile or bifunctional epoxide. In one preferred embodiment, the bifunctional electrophile is 1,6-dibromohexane.

One advantageous feature of the invention is the broad range of the substituent, E or R1, on the 1-N of 2-vinyl-4, 5-dicyanoimidazole; and the role of E or R1 on the polymer derived from the above monomer. The location of E, R1 on the monomer makes it unlikely that even moderately bulky groups will interfere with the vinylic polymerization by either free radical or anionically induced polymerization. The thermal polymerization of 1-H-2-vinyl-4,5- dicyanoimidazole is a special case and is described separately. Thus, R1 can be nearly any organic group which can be put on by reaction with an electrophilic reagent. In some cases, R1 might be chosen to afford certain solubility characteristics to the polymer. For example, if R1 is a relatively long chain such as nonyl, the polymer would be solubilized in the less polar organic solvents. If R1 is a small group such as methyl, its steric influence on polymer properties and backbone would be minimized. It is noteworthy that the presence of any group R1 makes the molecule behave differently from 1-H because of the acidity of the H. Attempts to polymerize 1-H-2-vinyl-4,5-dicyanoimidazole by anionic methods would lead to deprotonation and no polymerization.

In some cases, R1 could be chosen because of its ease of removal. However, unlike the protecting groups commonly employed on imidazoles, dicyanoimidazoles are not well protected by silylation or acylation. Silyl groups or acyl groups come off too readily. Additional protecting groups which may be useful in various applications are ethyl, isopropyl, sec-butyl, benzyl, methoxybenzyl, methyloxymethyl, carbamoyl, etc.

After polymerization and deprotection of the 1-N, this site is again available for functionalization. A variety of electrophiles could be chosen to attach groups which provide specialized functions. Such reactions on polymers are usually called grafting. Functional groups (E) which have been grafted onto polymers cover an exceedingly wide range of possibilities. They can allow catalytically active groups, fluorescent groups, hydrophobic or hydrophilic modifiers, etc. Another important use of the 1-N site is its potential for crosslinking. A bifunctional electrophile such as 1,6-dibromohexane or bifunctional epoxides commonly used for urethane crosslinking, could be applied to this system.

Methods for forming the novel monomers and polymers of the invention will now be described.

There are two general routes to prepare the 4,5-dicyanoimidazoles from diaminomaleonitrile (DAMN). It is possible to start from an electrophile which is an acid or masked acid such as an orthoformate. This method was originally described by Woodward in U.S. Pat. No. 2,534,331 (1950), which is incorporated herein by reference in its entirety. Alternatively, one can start from a mono Schiff base and carry out oxidative ring closure. This is similar to a method as described in U.S. Pat. No. 4,220,466 (1980), by Patel, which is incorporated herein by reference in its entirety.

In one embodiment, the methodology begins by reaction of DAMN with acrolein or simple substituted acroleins such as methacrolein and crotonaldehyde. The oxidation of these acyclic monoanils leads directly to 2-vinyl-4,5-dicyanoimidazoles. The parent monomer of this family is 1-H-2-vinyl-4,5-dicyanoimidazole, and has the empirical formula $C_7H_4N_4$. It contains approximately 39% nitrogen by weight. These initial materials, acrodamn, and substituted variations crotodamn and methacrodamn, are prepared by processes given directly below, also described in U.S. Pat. No. 5,712,408 (Rasmussen et al Jan. 27, 1998), incorporated herein by reference in its entirety. See also PCT/US97/14093, which is PCT of U.S. Pat. No. 5,712,408, also incorporated by reference.

N-(cis-1,2-dicyano-2-aminovinyl)-2-butenimine (Crotodamn)

Figure 7:
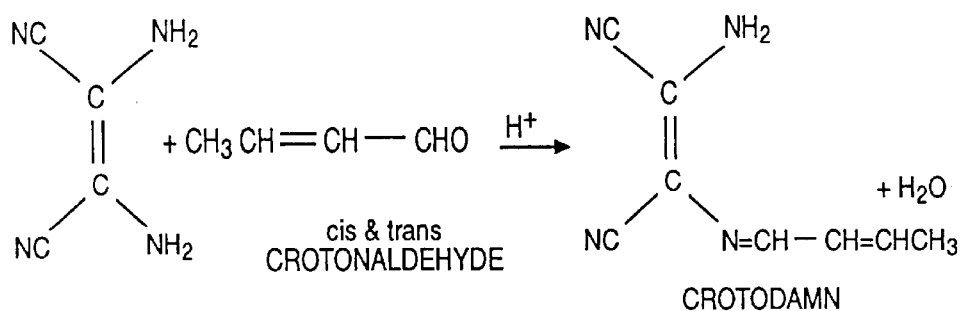
FIG. 7 is an illustration of a basic reaction for preparing N-(cis-1,2-dicyano-2-aminovinyl)-2-butenimine (crotodamn), a starting material used to form monomers and polymers of the invention.

A solution was prepared comprising 3.3 milliliters (40.0 mmol) of crotonaldehyde and 10 drops of 1 molar hydrochloric acid in 40 milliliters of tetrahydrofuran. The solution was cooled to a temperature of approximately 0° C. A second solution was prepared comprising 4.015 grams (37.1 mmol) of diaminomaleonitrile in 100 milliliters of tetrahydrofuran, also cooled to a temperature of approximately 0° C. The diaminomaleonitrile solution was slowly added to the solution containing the crotonaldehyde while stirring. After 5 minutes, the mixed solution was poured over 500 milliliters of ice cold hexane. The resulting precipitate was collected and dried and yielded 3.867 grams of a white, fluffy powder (FIG. 7). The mother liquor was stripped down to give an additional 1.862 grams of a light yellow powder, providing a total yield of approximately of 96.5 percent. The powder was recrystallized from ether/hexane to give white/light yellow powdery crystals. Upon sublimation at reduced pressure, clear yellow needle-shaped crystals were formed. The product exhibited a melting point of approximately 109° C. to 112° C., infrared characteristics 3457, 3349 (—NH2), 2950 (alkyl), 2239, 2206 (—CN), 1638, 1620, 1606, 1587, 1563, 1370, and 985 cm–1. NMR analysis using DMSO solvent revealed δ1.9 (d, 3H), 6.3 (m, 1H), 6.6 (m, 1H), 7.6 (s, 2H), and 7.9 (d, 1H). The calculated product was analyzed to have a formula $C_8H_8N_4$ corresponding to the following weight percents: carbon, 60.0; hydrogen, 5.0; and nitrogen, 35.0. Actual analysis revealed: carbon, 60.8; hydrogen, 5.1; and nitrogen, 33.9, verifying the formula of the product N-(cis-1,2-dicyano-2-ethylaminovinyl)-2-butenimine (Crotodamn).

N-(cis-1,2-dicyano-2-aminovinyl)-2-propenimine (Acrodamn)

Figure 5:
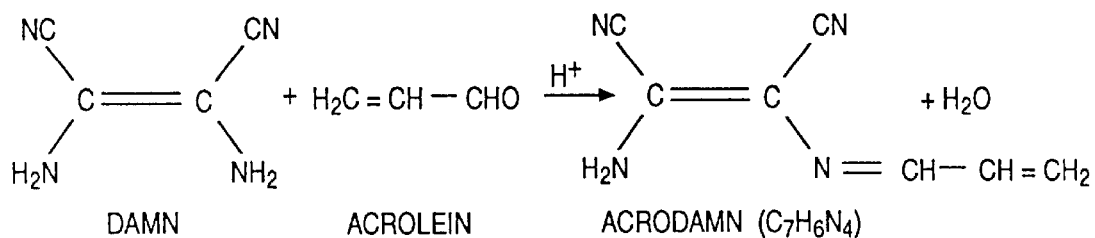
FIG. 5 is an illustration of a basic reaction for preparing N-(cis-1,2-dicyano-2-aminovinyl)-2-propenimine (acrodamn), a starting material used to form monomers and polymers of the invention.

A similar method of preparation was conducted using the acrolein precursor to prepare N-(cis-1,2-dicyano-2-aminovinyl)-2-propenimine (FIG. 5). This product exhibited infrared pattern at 3416, 3297, 3170 evidencing an amine (—NH$_2$), 2232, 2214 (—CN), 1630, 1587, 1381, 1350, 992, and 965 cm$^{-1}$. NMR analysis conducted in DMSO revealed δ5.9 (d, 1H), 6.1 (d, 1H), 6.6 (m, 1H), 7.9 (s, 2H), and 8.0 (d, 1H). Compositional analysis for the $C_7H_6N_4$ product was calculated on a weight percent basis to be carbon, 57.5; hydrogen, 4.1; and nitrogen, 38.4. Actual analysis revealed: carbon, 57.8; hydrogen, 4.4; and nitrogen, 38.2, evidencing a compound of the formula N-(cis-1,2-dicyano-2-aminovinyl)-2-propenimine (Acrodamn).

N-(cis-1,2dicyano-2-aminovinyl)-2-methylpropenixine (Methacrodamn)

Figure 6:
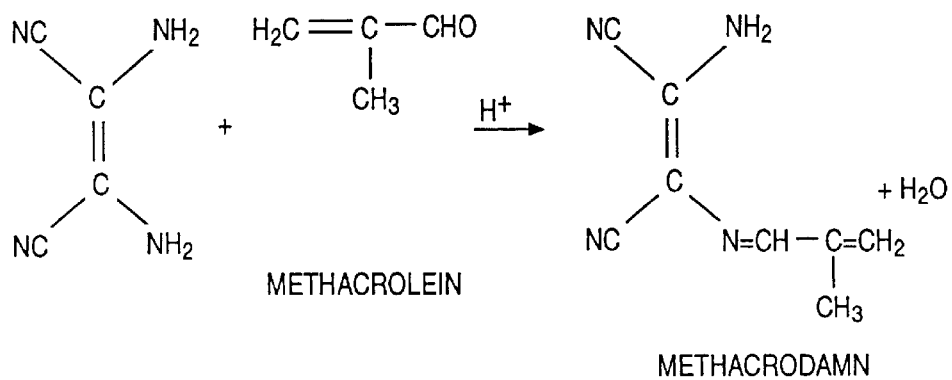
FIG. 6 is an illustration of a basic reaction for preparing N-(cis-1,2-dicyano-2-aminovinyl)-2-methyl-propenimine (methacrodamn), a starting material used to form monomers and polymers of the invention.

A compound designated as N-(cis-1,2-dicyano-2-aminovinyl)-2-methylpropenimine was also prepared utilizing the methacrolein precursor (FIG. 6). The resulting product was found to have a melting point of approximately 118° C. to 120° C. It exhibited infrared values at 3451, 3418, 3306 evidencing an amine (—NH$_2$), 2959 (-alkyl); 2244, 2207 (—CN), 1614, 1595, 1389, 1350, and 909 cm$^{-1}$. Analysis by NMR in DMSO solvent revealed δ1.9 (s, 3H), 5.76 (s, 1H), 5.80 (s, 1H), 7.7 (s, 2H), and 7.9 (s, 1H). The product had a calculated general formula of $C_8H_8N_4$ with constituents present in the following weight percents: carbon, 60.0; hydrogen, 5.0; and nitrogen, 35.0. The actual analysis revealed carbon, 60.3; hydrogen, 5.2; and nitrogen 34.3, evidencing a compound of the formula N-(cis-1,2-dicyano-2-aminovinyl)-2-methylpropenimine.

Figure 8:
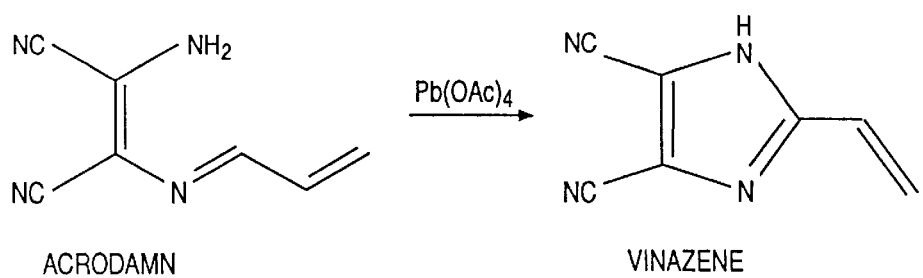
FIG. 8 is an illustration of a basic reaction for preparing 2-vinyl-4,5-dicyanoimidazole given the name Vinazene (trademark). Here, acrodamn of FIG. 5 is oxidized to 1-H-2-vinyl-4,5-dicyanoimidazole.

In accordance with the above, the methodology makes use of the unsaturated monoanils of DAMN as starting materials for the preparation of 2-vinyl-4,5-dicyanoimidazoles. The monoanils can be oxidatively ring closed using oxidants such as lead tetraacetate to afford the vinyl imidazoles. For example, the acrodamn compound is oxidized to 1-H-2-vinyl-4,5-dicyanoimidazole as shown in FIG. 8. For discussion purposes, this oxidation product has been given the trivial name "Vinazene" (trademark).

It is somewhat surprising that this oxidation method can be applied to acrodamn to effect oxidative ring closure to produce 2-vinyl-4,5-dicyanoimidazole without inducing polymerization. The mechanism probably involves equilibrium cyclization from which aromatization proceeds by irreversible dehydrogenation. The unoptimized yields for this oxidation, which must be run carefully, are over 80%.

Figure 9:
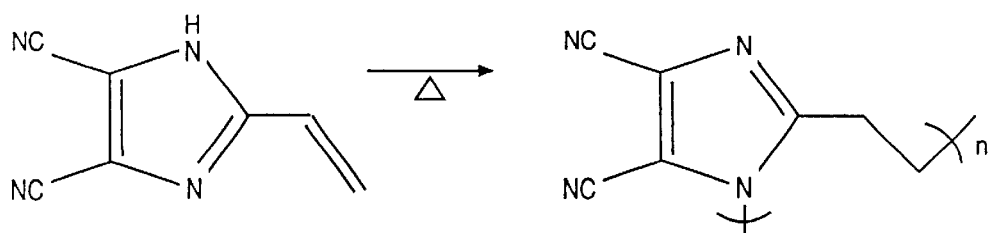
FIG. 9 shows the monomer of FIG. 8 under thermolysis to achieve Michael-type addition polymerization to form the polymer with the imidazole "in-chain". The linkage is achieved through the 7 carbon and the 1 nitrogen.
Figure 10:
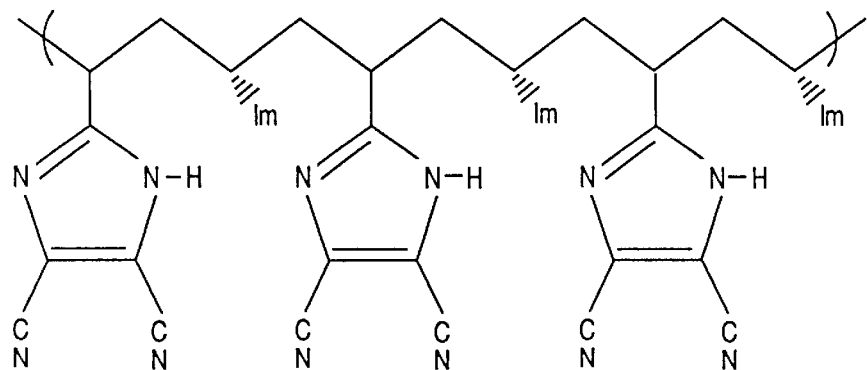
FIG. 10 shows the monomer of FIG. 8 after free radical polymerization. Here, alternate imidazole rings are abbreviated as Im, for clarity. The rings are pendant to a backbone by linkage at the 2 position carbon.

Detailed characterization data for this new compound are provided later below. This parent monomer polymerizes in two ways. Under thermolysis it undergoes Michael-type addition polymerization to form the polymer with the imidazole "in-chain" as shown in FIG. 9. DSC and TGA are given below. If however the same monomer is treated with free radical initiator, such as benzoyl peroxide, a vinylically derived free radical polymerization is induced in which the cyanoimidazole rings are pendant to a polymethylene backbone, as shown in FIG. 10. In this polymer the acidic hydrogen at the one position remains and the polymer can be dissolved and processed by dissolving it in base. This backbone has opportunity for 1,3 hydrogen bonding to occur both interchain and along the chain repeats.

Figure 11:
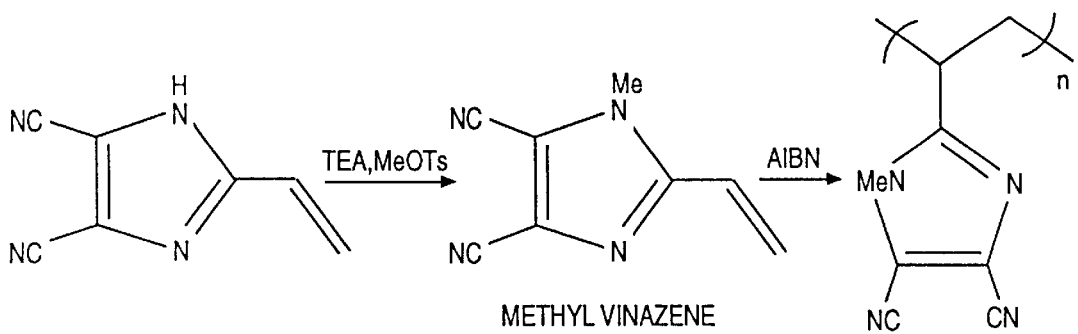
FIG. 11 shows the monomer alkylated to form methyl Vinazene (trademark), also 1-methyl-2-vinyl-4,5 dicyanoimidazole. Then the 1-protected monomer undergoes vinylic polymerization by AIBN initiator.

Another aspect of the invention concerns the fact that the monomer described above, can be alkylated or otherwise protected without inducing polymerization. Thus for example, it can be methylated as shown in FIG. 11. The resulting 1-protected monomer, methyl Vinazene, also undergoes vinylic polymerization, for example by the initiator AIBN as in FIG. 11. In this example, a polymer of viscosity average molecular weight 140,000 was prepared at 65° C. in acetonitrile. Examples of polymer stability assayed by thermogravimetric analysis are provided in the accompanying data.

This same monomer can be polymerized by anionic initiation, for example, by the use of fluorenyl lithium. This initiator, which is known to initiate acrylonitrile, but not styrene, places the monomer among those polymerized by mild anionic methods. This placement suggests the possibility of readily forming copolymers and perhaps block copolymers of this and related monomers, with styrene, acrylonitrile, and other large volume monomers which are initiated under similar conditions.

Figure 12:
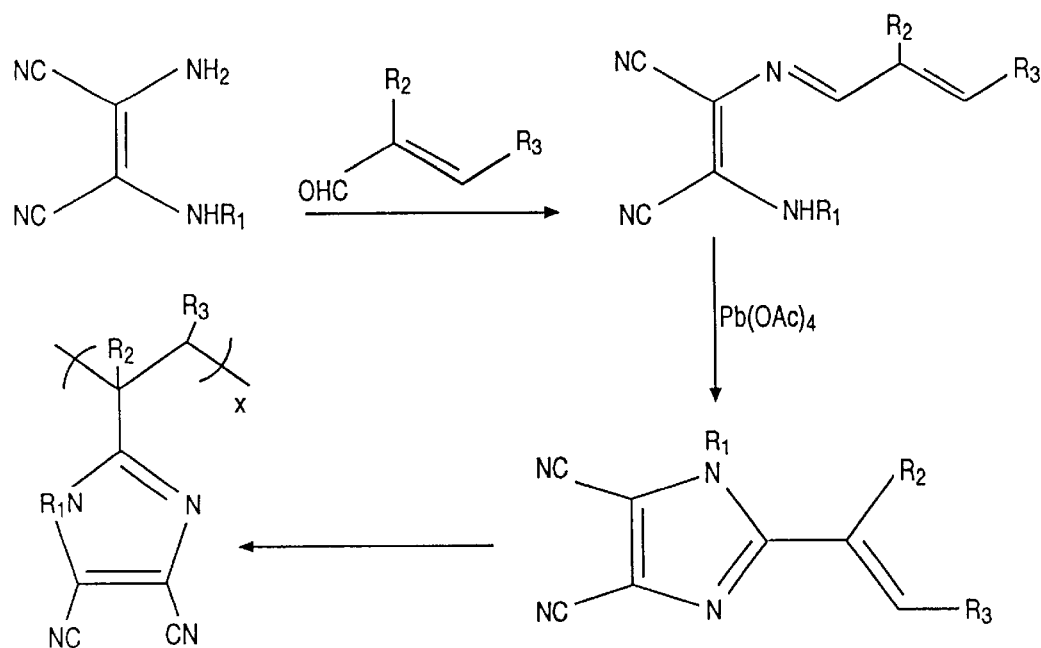
FIG. 12 shows that the varying substituents R1, R2 and R3 are usable to form starting materials, similar to that illustrated by FIGS. 5–7; and to form monomers and polymers carrying such substituents.

The monomer(s) are easily modified by using various substituents (R1), at the 1-nitrogen as described above. However, by varying the starting materials, the substituents R2, and R3 can also be varied, as per FIG. 12.

Figure 13:
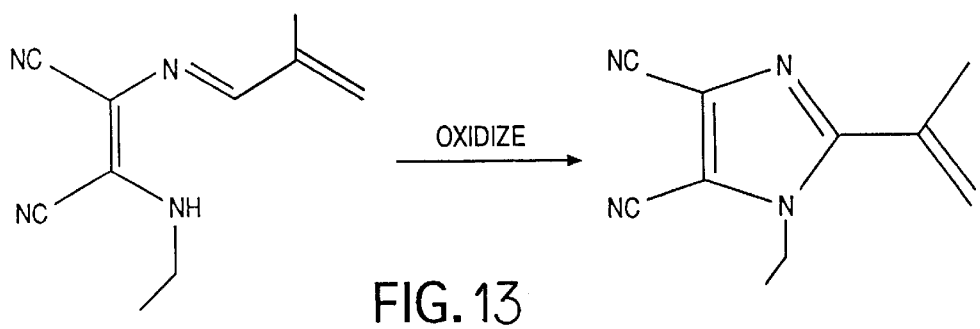
FIG. 13 shows an example of forming a cyclic dicyanoimidazole compound using Schiff base derived from N-ethyl DAMN (diaminomaleonitrile).

As described above, there were prepared Schiff base derivatives of DAMN using different aldehydes, for example, methacrodamn, R2=methyl, R3=H; crotodamn, R2=H, R3=methyl. Schiff bases derived from N-ethyl DAMN (R1=ethyl) can also be oxidized by the methods described above to afford the corresponding cyanoimidazole derivatives. Thus, for example, N-ethylmethacrodamn is oxidized to 1-ethyl-2-[1-methyl vinyl]-4,5-dicyanoimidazole, as per FIG. 13.

The new polymers are useful in applications which call for higher thermal and oxidative stability than conventional vinylic polymers. The nitrogen content of the parent monomer, 1-H-2-vinyl-4,5-dicyanoimidazole, and its polymers is, for example, 39% by weight. This high nitrogen content, along with the intrinsic stability of the imidazole ring system, gives the polymers potential for providing inhibition of flammability, higher softening temperatures, and greater char yields than conventional materials. A summary of the advantages found in pursuing applications for these new polymers are described here below.

There is a moderate cost structure. Synthesis of monomers occurs in one or two steps from starting materials that are nearly commodities. Although polymers directly derived from acrolein are uncommon, this material has a current world production estimated at 125,000 tonnes per year. DAMN is a stable solid, marketed by Nippon Soda Co. at moderate prices. The monomers polymerize very readily by thermal or chemical initiation at very moderate temperatures to afford polymers. These polymers have high thermal stability and they decompose with low gas evolution. Once the cyclization to imidazole takes place, the heteroaromatic stability long associated with this ring system in polymer chemistry provides very robust materials. The stoichiometric composition of the materials, with their very high nitrogen and low hydrogen content, suggests their use as flame retardants, protective coatings, and in specialty materials which demand high oxidation resistance.

The monomers or the polymers are easily modified. The family of derivatives appears to be limited only by the range of electrophiles which will readily attach to the 1-N. Since cyanoimidazole anion is a good leaving group, the 1,3 sites can function together in a catalytic mode for the transfer of attached groups. Grafting reactions should also be very facile. The cyano groups can be hydrolyzed before or after polymerization to afford amides or carboxylic acid. This may prove to be a highly economical route to cation exchange resins or metal ion sequestering polymers.

SYNTHESIS OF MONOMERS AND POLYMERS

2-Vinyl-4,5-dicyanoimidazole

The acrodamn, prepared as per the earlier described method, was used in this present synthesis. The acrodamn (7.00 g) was dissolved in 150 ml of distilled acetonitrile, yielding an orange solution. A solution of 22.5 g of lead (IV) tetraacetate and 300 ml of distilled acetonitrile was placed in a room temperature water bath. The acrodamn/acetonitrile solution was poured, in one portion, into the lead (IV) tetraacetate solution. The colorless lead solution immediately darkened to an orange-red solution and a white, voluminous precipitate with a metallic sheen appeared. The solution was allowed to stir for 10 minutes, and then filtered. The resulting precipitate was washed via filtration until no more color was liberated in the filtrate. The filtrate was then rotovapped and stripped with a vacuum pump. To the resulting residue, 400 ml of ether was added and allowed to stir overnight. The ether solution was filtered and rotovapped to yield 5.63 g of 2-vinyl-4,5-dicyanoimidazole (82%) as a reddish solid. This crude product shows very small traces of unidentified impurity and may be purified by dissolving in a minimum of ethyl acetate, pouring the ethyl acetate into ether, filtering the precipitate, and evaporating the filtrate to recover the product for essentially quantitative recovery.

Mp 168–170° C., IR 3310 (—NH), 2241 (—CN), 1640, 1619, 1510, 1431, 1405, 1300, 1069, 1003 cm−1; NMR (DMSO-$d_6$) $\delta 5.2$ (dd, J=10.95, 2.06 Hz, 1H), 5.9 (dd, J =17.61,2.06 Hz, 1H), 6.5 (dd, 17.61, 10.95 Hz, 1H, $H_\alpha$).

1-Methyl-2-vinyl-4,5-dicyanoimidazole

To a solution of 0.602 g (4.17 mmol) of 2-vinyl-4,5-dicyanoimidazole in distilled THF (15 mL) at 0° C. under nitrogen was added slowly while stirring 0.22 mL (2.32 mmol) of dimethyl sulfate and 0.60 mL (4.30 mmol) triethylaminine via syringe. The reaction solution was allowed to come to room temperature and was stirred for 15 hours. The reaction solution was concentrated down under a stream of nitrogen and dissolved in 10 mL $CH_2Cl_2$. This solution was washed twice with a 10% solution of NaOH and twice with a saturated solution of NaCl. $CH_2Cl_2$ was stripped off, leaving a brown oil. This oil was dissolved in approximately 1 mL of THF and precipitated out in hexane. The precipitate was vacuum filtered and dried to yield 0.345 g (52.4% yield) of a light brown, fluffy powder. This powder was dissolved in 100 mL of ether and vacuum filtered to remove undissolved particles. 20 mL of hexane was added to the ether solution, and the solution was cooled to 0° C. White, needle-shaped crystals were formed and vacuum filtered.

Mp 96–99° C.; ir 2237 (—CN), 1492, 1464, 1420, 1378, 1328, 986, 948, and 765 cm–1; nmr (DMSO-$d_6$) δ 3.8 (s, 3H, —$CH_3$), 5.8 (dd, J=10.89, 1.09 Hz, 1H), 6.3 (dd, J=17.35, 1.09 Hz, 1H), 6.9 (dd, J=17.35, 10.89, 1H, $H_\alpha$).

1-Ethyl-2-Vinyl-4,5-Dicyanoimidazole

A flask equipped with a magnetic stirbar was charged with 6.26 g of 2-vinyldicyanoimidazole. To this, 75 ml of distilled THF and 6.1 ml of triethylamine were added with stirring. After 5 minutes stirring, 5.7 ml of diethyl sulphate was added. This mixture was allowed to stir for 2 days. Analysis by TLC (50/50 hexane/ethyl acetate, UV visualization) showed the reaction was complete (starting material rf 0.3, product rf 0.6). The THF solution was rotovapped and the residue was dissolved in ethyl acetate. The ethyl acetate was washed with 10% aqueous sodium hydroxide. The combined aqueous layers were back extracted with methylene chloride. The combined organic layers were dried with magnesium sulphate and rotovapped to dryness. The crude residue was triturated with ether. The ether extracts were rotovapped and the residue recrystallized with ether/hexanes to yield 3.124 g of the product, mp 66–70° C. as yellow needles. A second crop yielded 1.72 g for a combined yield of 65%.

H NMR: 6.95δ, 1H (dd J=17.04, 10.99 Hz); 6.36δ, 1H (dd J=17.04, 1.38 Hz); 5.81δ, 1H (dd J=10.99, 1.38 Hz); 4.28δ, 2H (q J=7.14 Hz); 1.33δ, 3H (t J=7.14 Hz)

Poly[-(1-methyl-4,5-dicyano-2-imidazolyl) ethylene]

Poly[1-(4,5-dicyano-1-methyl-2-imidazolyl) ethylene]
Free Radical Initiation

1-Methyl-2-vinyl-4,5-dicyanoimidazole (0.356 g, 2.25 mmol) and AIBN (0.005 g, 0.03 mmol) were added to 0.5 mL distilled MeCN in a 10 mL thick-walled test tube with a side arm and stir bar. The test tube was covered with a septum and connected to a vacuum/nitrogen line via the side arm. After cooling the test tube to –78° C. in dry ice/acetone, the contents of the test tube were evacuated and filled with nitrogen three times. The test tube was allowed to come to room temperature and then placed into a 60–65° C. oil bath for 16 hours. Upon removal from the oil bath, the reaction mixture was a brown/yellow viscous material. Upon removal of THF, a brown/yellow glassy solid resulted which was somewhat soluble in MeCN and DMSO, but not THF or $H_2SO_4$: nmr (DMSO) δ 1.6, 2.0, 2.8, 3.6; viscosity [η]=0.59 dL/g. The product was as per FIGS. 4 and 4(A).

Anionic Initiation

1-Methyl-4,5-dicyano-2-vinylimidazole (0.100 g. 0.633 mmol) was added to 1.0 mL of distilled THF in a 10 mL thick-walled test tube with a side arm (oven dried). Fluorene (0.055 g, 0.33 mmol) was added to 1.0 mL of distilled THF in a separate 10 mL side arm test tube. Both test tubes were covered with a septum and connected to a vacuum/nitrogen line via their side arms. The test tubes and their contents were cooled to –78° C. in a dry ice/acetone bath and were evacuated and filled with nitrogen three times. While still at –78° C., 0.2 mL of a 1.58 M solution of butyllithium was added to the fluorene solution which immediately turned an orange color. A syringe was used to transfer 0.1 mL of the fluorenyl lithium solution to the test tube with 1-methyl-4, 5-dicyano-2-vinylimidazole. The reaction mixture immediately turned a darker color and a brown precipitate formed. Methanol (1.0 mL) was added to quench the anion and the solution turned an orange color. The precipitate was filtered and washed with ether yielding a light orange powder which was insoluble in THF but still soluble in acetonitrile; NMR δ 1.6, 2.0, 2.8, 3.6, 8.8 (partial hydrolysis of nitriles). The product was as per FIGS. 4 and 4A.

Poly [1-(1-H-4,5-dicyano-2-imidazolyl)ethylene]

To a solution of 280 mg of 2-vinyl-4,5-dicyanoimidazole in 2 ml of DMF was added 7 mg of benzoyl peroxide. The solution was degassed using three cycles of the freeze-pump-thaw method, and placed in a constant temperature bath (120° C.) overnight (12 hours). The solvent was removed by high vacuum evacuation. The polymer was characterized by NMR, and shown to contain a very small portion of monomer, as well as residual solvent. H NMR (DMSO-$d_6$) δ 1.7 (v br). The product was as per FIG. 10.

Synthesis of Michael-type Polymer

Figure 14:
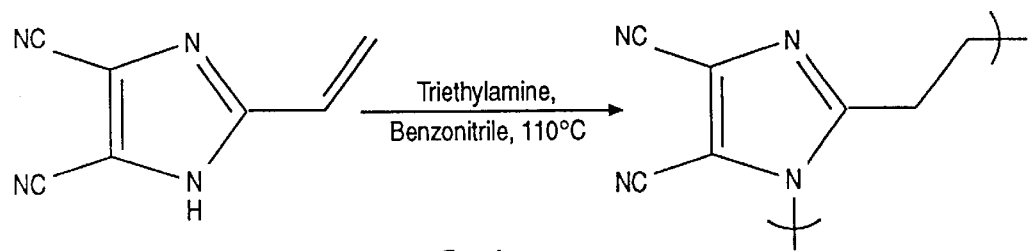
FIG. 14 shows a reaction to form a Michael-type polymer using triethylamine and benzonitrile.

A test tube fit with a schlenk sidearm was charged with 0.23 g (1.59 mmol) or 4,5-dicyano-2-vinylimadazole. A magnetic spine vane was added and the test tube was sealed with a septum. Via cannulation, 2 ml of benzonitrile was added to the test tube and 0.26 ml (1.87 mmol, 18% excess) of triethylamine was added via a syringe. The test tube was placed in a hot oil bath (110° C.) and allowed to stir overnight. After overnight heating and stirring, the heat bath was removed and the contents of the schlenk test tube were rinsed into a round bottom flask with acetone. The solution was rotovapped until no more solvent was liberalized and then placed in a hot water bath (65° C.) under high vacuum. This treatment afforded a dark tacky solid. The process and product polymer are as per FIG. 14.

Characterization of Monomers and Polymers

Figure 15:
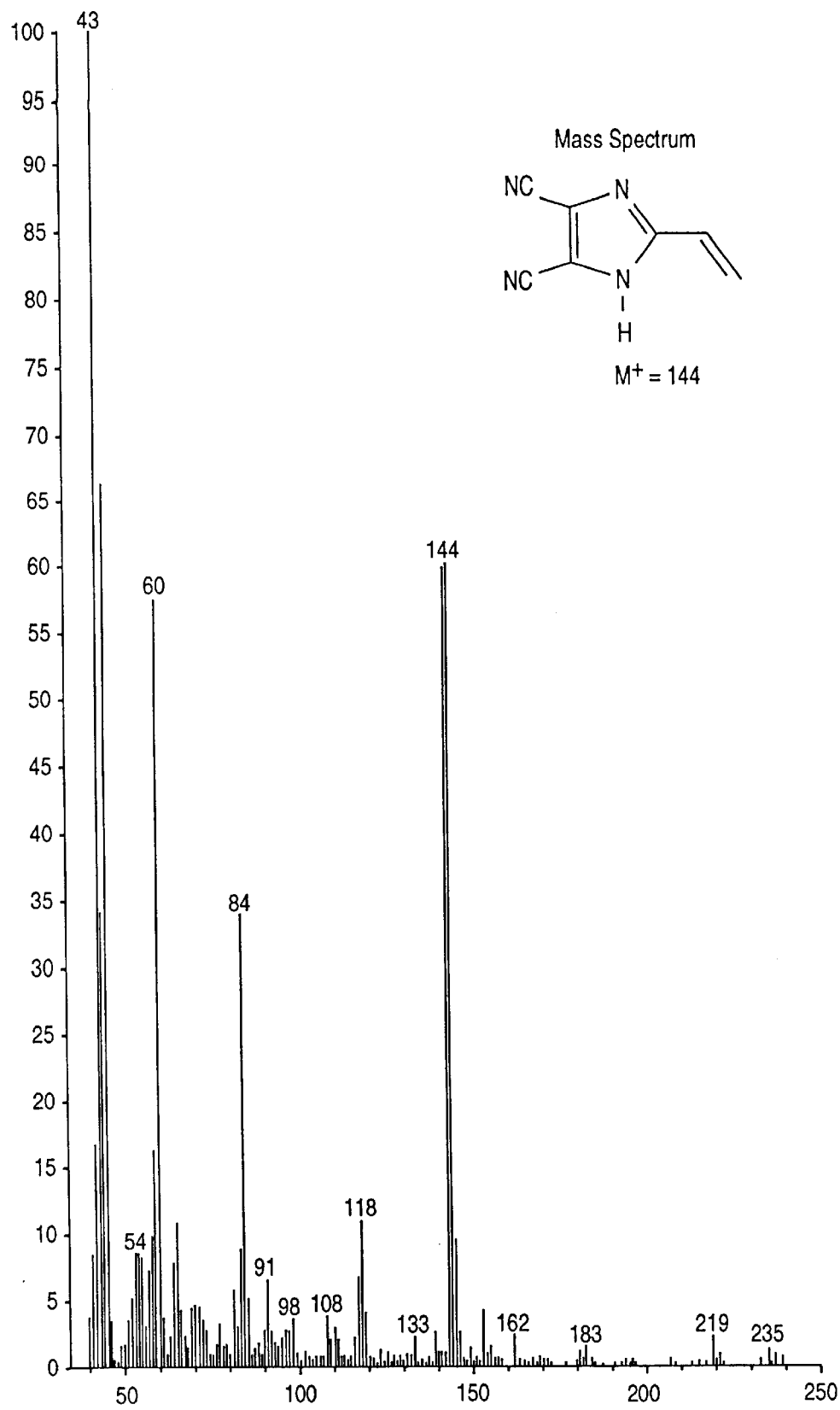
FIG. 15 is a mass spectrum of 1-H-2-vinyl-4,5 dicyanoimidazole.
Figure 16:
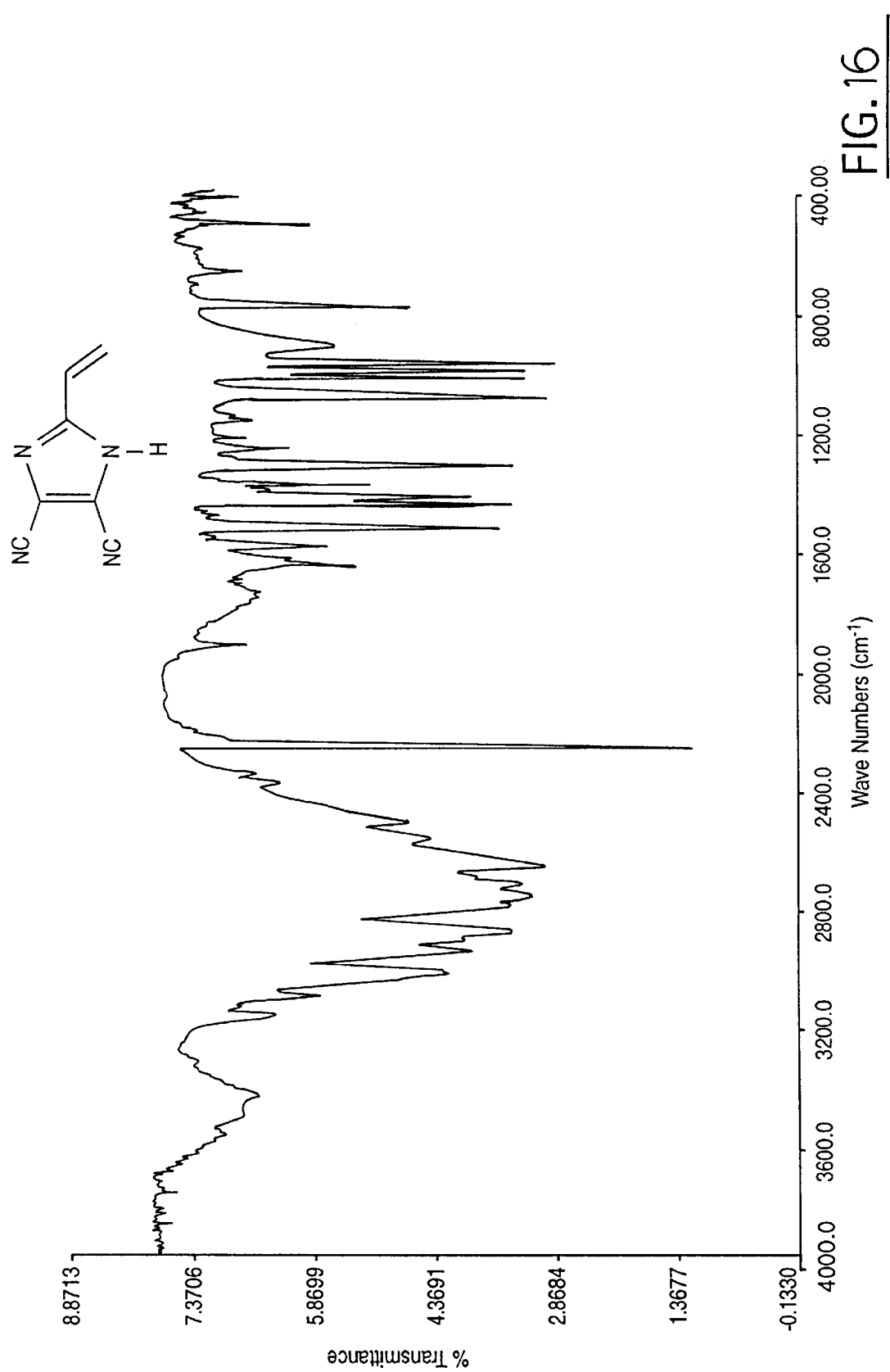
FIG. 16 is a KBr-type IR spectra of 1-H-2-vinyl-4,5 dicyanoimidazole.
Figure 17:
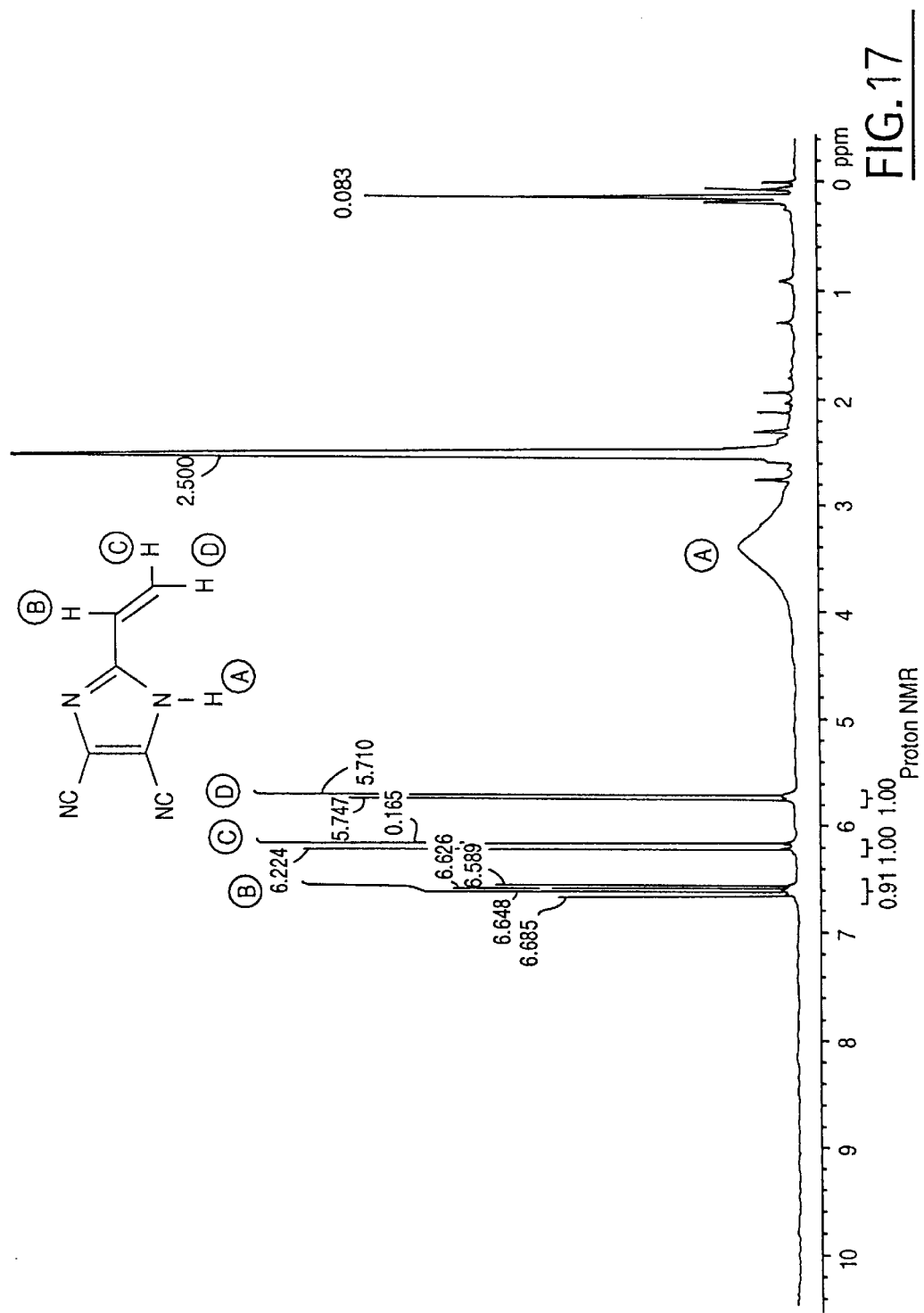
FIG. 17 is a proton-type NMR of 1-H-2-vinyl-4,5 dicyanoimidazole.

FIGS. 15, 16 and 17 are respectively Mass, Infrared, and Proton NMR spectra of 2-vinyl-4,5-dicyanoimidazole.

FIG. 15 is the mass spectrum for Vinazene. The parent peak occurs at 144, the mass necessary for $C_7H_4N_4$. A relatively intense peak occurs at 143, corresponding to loss of hydrogen from the 1-position of the aromatic ring. A peak occurs at 108, corresponding to loss of a CN functionality.

FIG. 16 shows the infrared spectrum of Vinazene. The hydrogen-bonding pattern from approximately 3200 to 2400 is consistent with a 1,3-hydrogen-bonding pattern from a 2-substituted dicyanoimadazole ring. A sharp peak at 2250 is indicative of the nitrile.

FIG. 17 shows the proton nuclear magnetic resonance spectrum of Vinazene. Three peaks at 5.7d, 6.2d, and 6.6d have three coupling constants between them. This is consistent with a singly-substituted vinyl group. These signals integrate to one proton each, consistent with the proposed structure. The peak at 2.5 is incompletely dueterated NMR solvent, DMSO. The peak at 3.3d is residual water in the NMR solvent.

Figure 18:
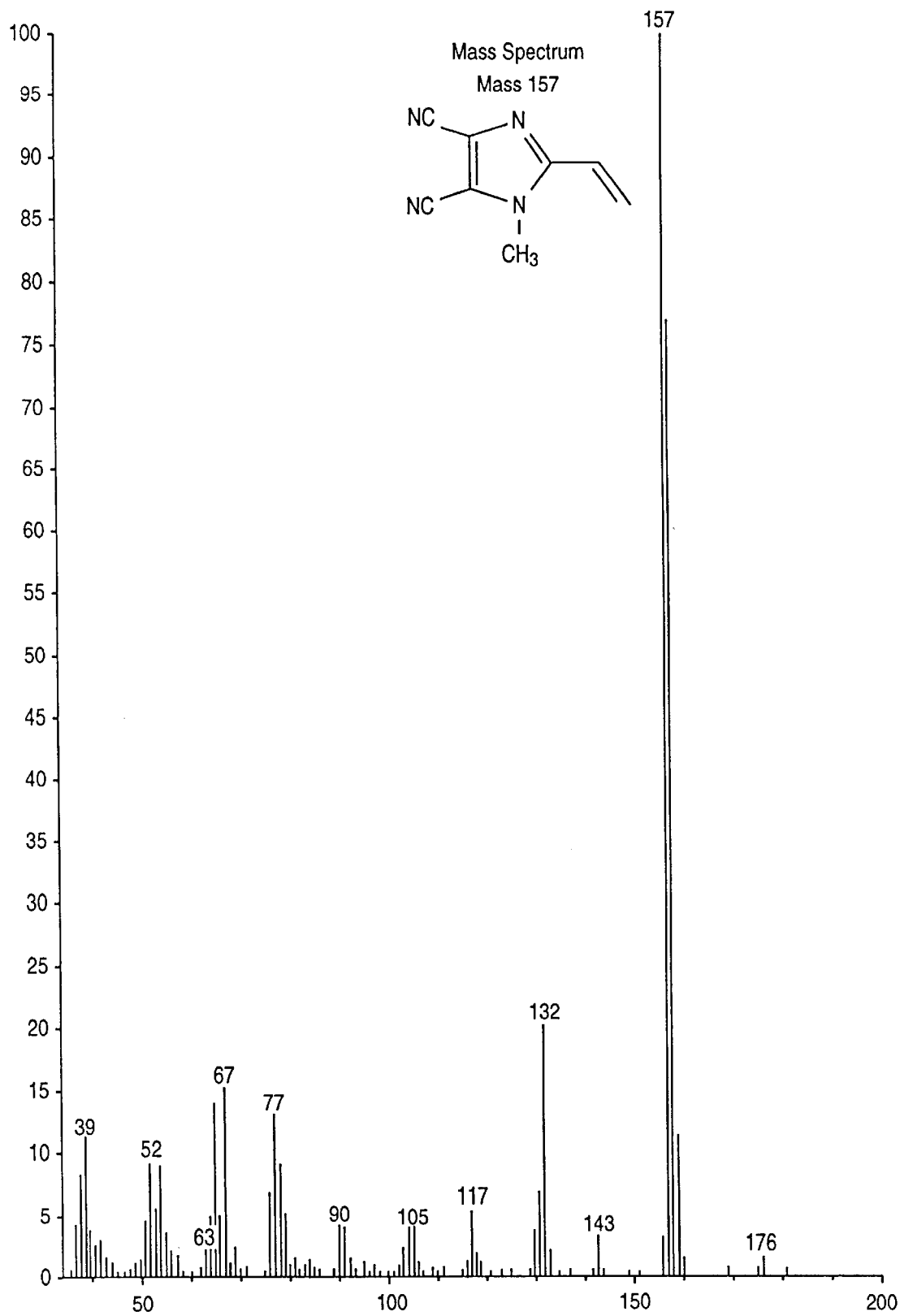
FIG. 18 is a mass spectrum of 1-methyl-2-vinyl-4,5 dicyanoimidazole.
Figure 19:
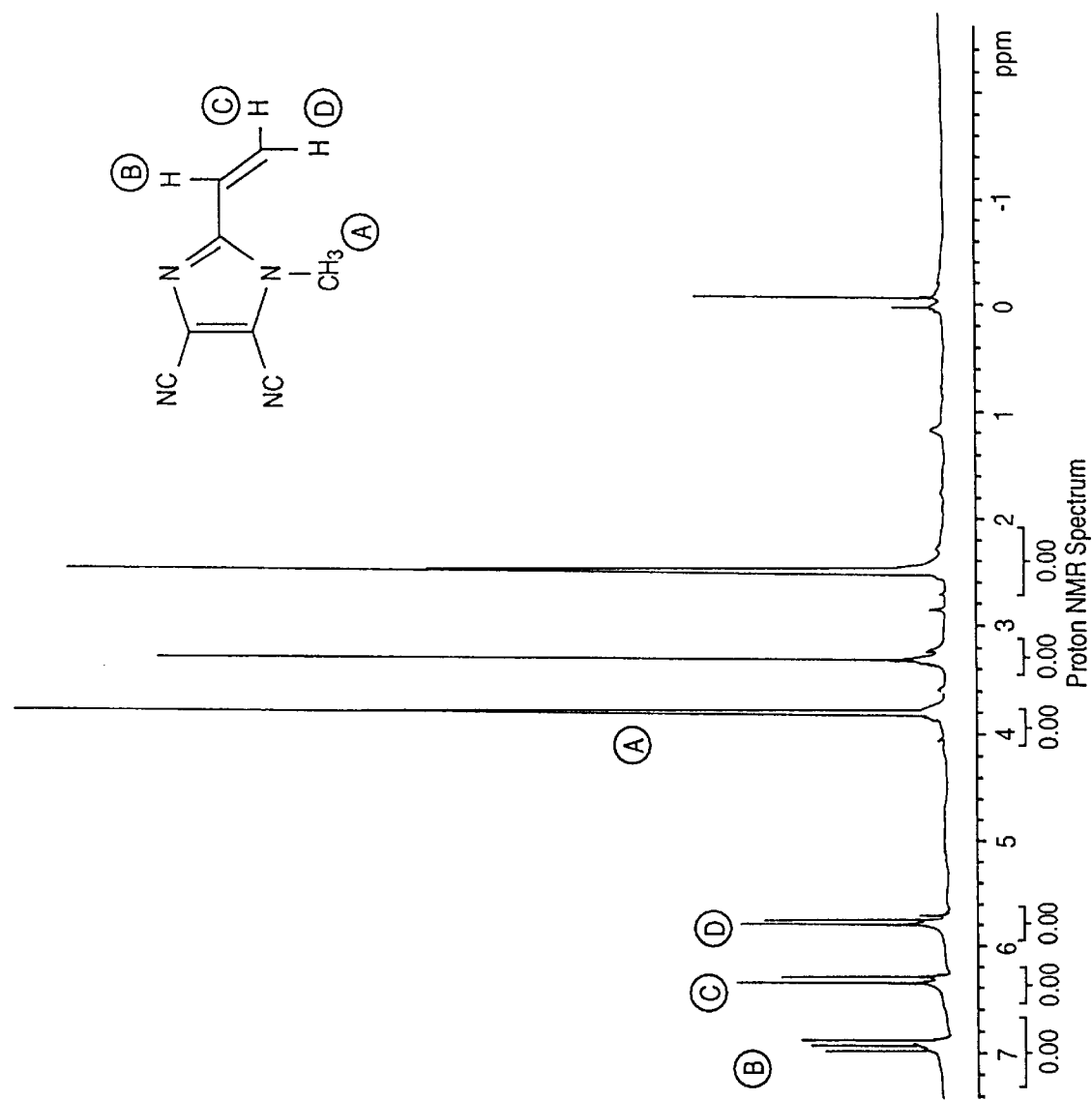
FIG. 19 is a proton-type NMR of 1-methyl-2-vinyl-4,5 dicyanoimidazole.

FIGS. 18 and 19 are respectively Mass and Proton NMR spectra of 1-methyl-2-vinyl-4,5-dicyanoimidazole. prepared by oxidation of acrodamn, which is the mono Schiff base of diaminomaleonitrile (DAMN) and acrolein. Since DAMN is the tetramer of hydrogen cyanide and acrolein is prepared by oxidation of propene, one can prepare 2-vinyl-4,5-dicyanoimidazole and its derivatives from readily available, moderately priced, starting materials. Once the oxidative cyclization occurs, the highly stable imidazole ring system prevents reverse reactions. In spite of high nitrogen content, these polymers lose very little HCN or cyanogen by thermal processes.

The dicyanoimidazole ring system is in conjugation with the 2-vinyl group, and this heterocycle has electron withdrawing effects similar to, but slightly weaker than, a simple cyano substituent. Thus, 2-vinyl-4,5-dicyanoimidazole behaves sterically like styrene and electronically like acrylonitrile or acrylic esters. The monomers polymerize very readily by free radical, or if substituted at 1-N, by anionic initiation to produce high molecular weight polymers. Unlike styrene, for which the vinylic group deactivates the ring, 2-vinyl-4,5-dicyanoimidazole is easily substituted at the 1-nitrogen by electrophiles before or after polymerization. Thus, an enormous variety of structural changes are feasible. In addition to the great flexibility offered by substitution at the 1-nitrogen, the nitriles of 4,5-dicyanoimidazole can also easily be modified to amides, carboxylic acids, or amines. Finally, the ease of polymerization of the 2-vinyl-4,5-dicyanoimidazole family of monomers suggests that copolymers will readily form.

High nitrogen, low hydrogen stoichiometries confer some special properties. Typically, such molecules are electron acceptors and have low base strength. They are often quite oxidation resistant and flame resistant. Certain combinations can have very FIG. 18 shows the mass spectrum for 1-methylvinazene. FIG. 15 is the mass spectrum for Vinazene. The parent peak occurs at 158, the mass necessary for $C_8H_6N_4$. A relatively intense peak occurs at 157, corresponding to loss of hydrogen from the 1-position of the aromatic ring. A peak occurs at 132, corresponding to loss of a CN functionality.

FIG. 19 shows the proton nuclear magnetic resonance spectrum of 1-methylvinazene. Three peaks at 7.0d, 6.4d, and 5.8d have three coupling constants between them. This is consistent with a singly-substituted vinyl group. An additional peak at 3.8d corresponds to the methyl group at the 1-position of the aromatic ring. The integrals on this spectra are incorrectly labeled to 0 each. The peak at 2.5 is incompletely dueterated NMR solvent, DMSO. The peak at 3.3d is residual water in the NMR solvent.

Figures 20, 21:
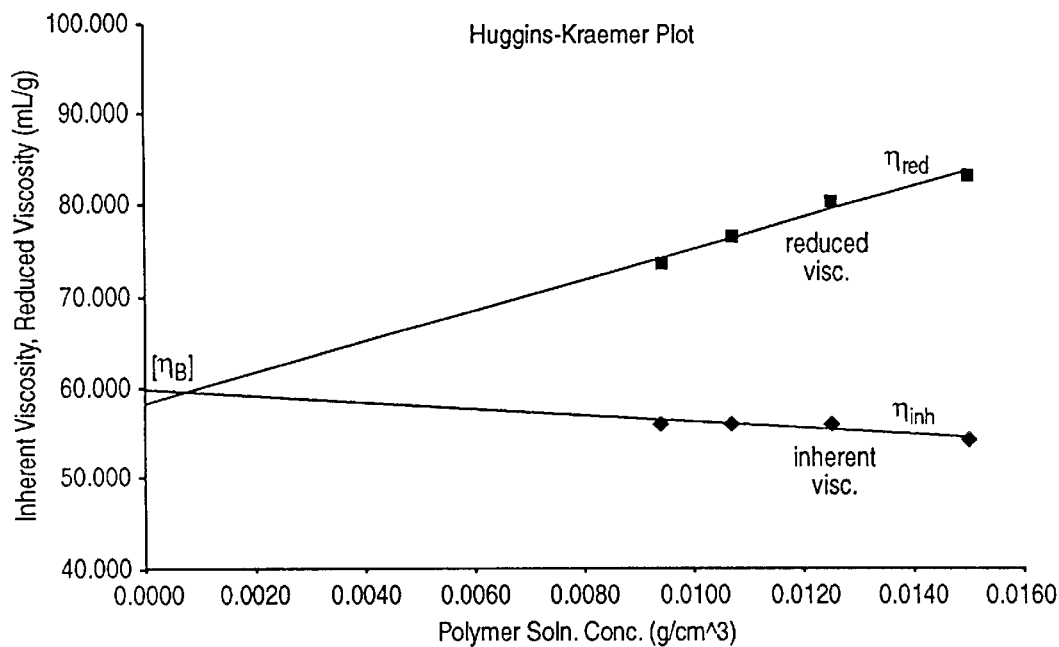
FIGS. 20 and 21 contain viscosimetric plots and data for molecular weight measurement of poly[1-(1-methyl-4,5-dicyano-2-imidazolyl)ethylene], also referred to as poly [methyl Vinazene].

FIGS. 20 and 21 contain viscosimetric plots and data for molecular weight measurement of poly[1-(1-methyl-4,5-dicyano-2-imidazolyl)ethylene], also referred to as poly [methyl Vinazene].

Figure 22:
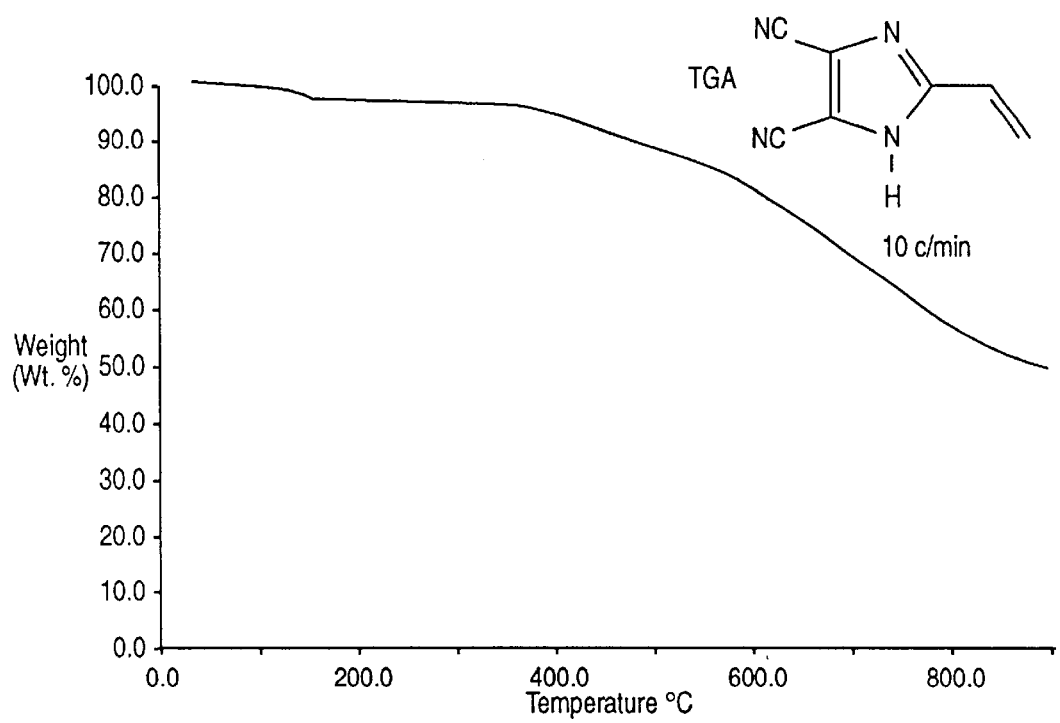
FIG. 22 shows the results of TGA (thermal gravimetric analysis) trace for the polymer formed by reaction in FIG. 9, a Michael-type poly(Vinazene).
Figure 23:
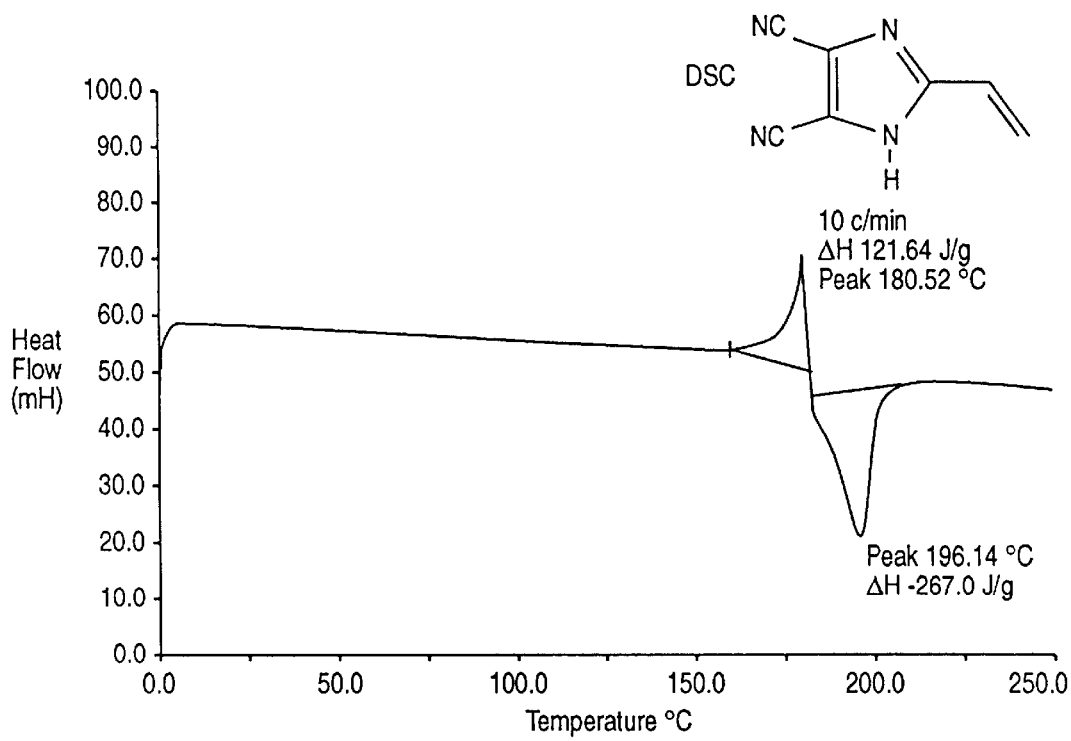
FIG. 23 shows the results of DSC (differential scanning calorimeter) analysis of Vinazene (trademark). The trace shows Vinazene forming Michael-type poly(Vinazene).

FIGS. 22 and 23 are respectively TGA and DSC plots for monomers and polymers.

Summarization, Applications, and Advantages

In polymer chemistry, there are relatively few families of useful vinylic monomers. Since the steric and electronic properties of a good monomer are quite well known, and a terminal vinyl group can only have two functionalities, one might be justified in assuming that all the simply prepared vinylic monomers have already been discovered. The present invention shows that this is not the case, based on a new family of monomers based on 2-vinyl-4,5-dicyanoimidazole. The parent monomer is high thermal stability as well. Thus, high nitrogen materials are replacing halogen compounds, which have undesirable environmental effects, as flame retardants. Low hydrogen content has another benefit. Compounds with numerous cyano groups do not readily evolve HCN when H content is low. In fact, total gas evolution can be low and char yield and nitrogen retention is remarkably high, even up to 900° C. under nitrogen.

To this point, there have been only a very limited number of polymers based on HCN. Polyacrylonitrile and polyacrylates are generally derivatives of HCN, and their place among the important polymers has been established for many years. However, certain compounds, such as cyanogen and the HCN tetramer, diaminomaleonitrile (DAMN), have not led to important polymers, in spite of considerable effort. Despite this, the present invention provides several key discoveries which allow the synthesis of a new family of polymeric materials. The present methodology starts by the reaction of DAMN with acrolein or simple substituted acroleins such as methacrolein and crotonaldehyde. These aldehydes are readily available and like DAMN itself, can be obtained at moderate prices in large quantities. The oxidation of these acylic mono anils leads directly to 2-vinyl-4,5-dicyanoimidazoles. The parent monomer of this family, 1-H-2-vinyl-4,5-dicyanoimidazole, has the empirical formula $C_7H_4N_4$, and contains 39% nitrogen by weight.

Additionally, there are some rather subtle inductive effects which control the reactions of DAMN. For example, if one attempts to prepare monomethyl DAMN by direct alkylation, it is difficult to stop the reaction at this stage. Instead, the first methylation activates the nitrogen towards a second addition, and the two methyls activate the second nitrogen towards addition of a third methyl. Thus, the result of slow, cold addition of one equivalent of methylation agent to dilute DAMN solution is trimethylDAMN. In sharp contrast to the methylation results, at zero degrees, with dilute acid catalyst, reaction of DAMN with acrolein forms only the mono-anil. The Schiff base formation at one nitrogen deactivates the second nitrogen towards forming the bis anil. On the other hand, the double bond, which now lies in conjugation to the DAMN end of the molecule, is highly activated.

Figure 24:
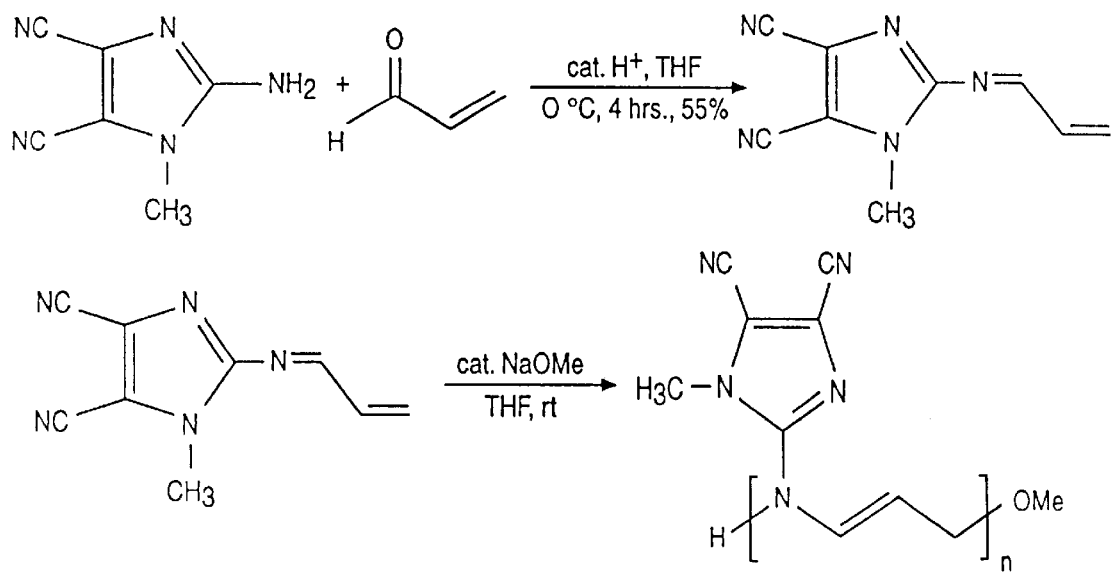
FIG. 24 is an illustration of a comparative reaction using a variation of the cyclic imidazole monomer. Here, the Schiff base of 1-methyl-2-amino-4,5-dicyanoimidazole is formed and it behaves very differently from Vinazene and N-methyl Vinazene.

To clarify the reactions of the Schiff base monomers, an anil was prepared from 1-methyl-2-amino-4,5-dicyanoimidazole (FIG. 24). This monomer has no nucleophilic sites which can react with the activated double bond and indeed behaves very differently from Vinazene and N-methyl Vinazene.

As stated earlier, there are two general routes to prepare the 4,5-dicyanomidazoles from DAMN. One can start from an electrophile, which is an acid or masked acid such as orthof ormate. Alternatively, one can start from a mono Schiff base and carry out oxidative ring closure. This latter method applied to acrodamn carries out an oxidative ring closure to produce 2-vinyl-4,5-dicyanoimidazole, without inducing polymerization. The mechanism probably involves equilibrium cyclization from which aromatization proceeds by irreversible dehydrogenation. The unoptimized yields for this oxidation, which must be run carefully, are currently at 82%. The acidic imidazole (pK~5) which results can be readily alkylated in high yield without interference from the other functional groups. This reaction is a prototype for the substitution of many other electrophiles onto the 1-position of the ring.

This present application refers to these monomers by the trivial names: vinazene (trademark), for the 1-H-2-vinyl-4, 5-dicyanoimidazole; and methyl Vinazene (trademark), etc., for its N-substituted derivatives. These monomers are fully characterized and are crystalline, air-stable, solids. However, they show a very interesting contrast in their thermal behavior. Vinazene has a potential Michael nucleophile at the 1-nitrogen, while methyl Vinazene does not. The DSC of Vinazene shows an exotherm following melting at 196° C., which is very similar to that of acrodamn, though not nearly as sharp. The TGA shows no weight loss in this region, and the ultimate char yield, starting from monomer, is very high.

This behavior closely mimics the behavior of the acyclic Schiff base derivatives of DAMN. One may interpret these results as evidence for a conjugate addition, step growth, type of polymerization in which the imidazole moiety is in the main chain, as shown below. However, Vinazene also polymerizes in a vinylic mode by earlier radical initiation, and this polymer has a very different structure and thermal signature in the TGA, in which the char yield is lower.

On the other hand, methyl Vinazene shows no exotherm in the DSC after the melting point, and no indication of thermally induced polymerization, at least to the limit of the scan. Thus, methyl Vinazene should behave like a normal vinylic monomer carrying an electron withdrawing group. The electron withdrawing character of dicyano substitution on imidazole is here known, but it is worth noting that dicyanoimidazole is nearly nine orders of magnitude more acidic than imidazole itself, pK~14.

Figure 25:
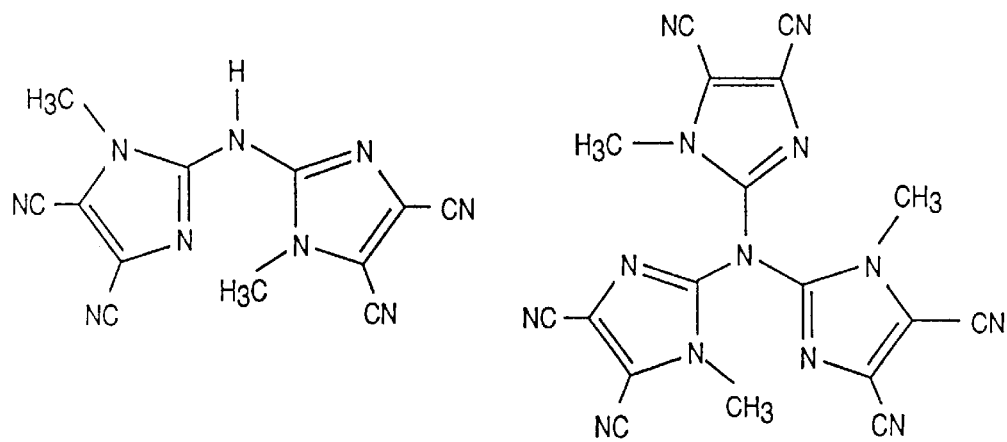
FIG. 25 shows another comparative dicyanoimidazole derivative which behaves differently from the monomers and polymers of the present invention.

These electron withdrawing effects have now been confirmed by several ancillary synthesis. The 1-methyl-2-fluoro-4,5-dicyanoimidzole can be used in nucleophilic aromatic substitution reactions. It reacts smoothly with most nucleophiles to allow the preparation of 2-substituted cyanoimidazoles of FIG. 25. The secondary amine has a pK~4, and the tertiary amine is nearly planar at nitrogen in its crystalline structure.

Thus, it is reasonable to place methyl Vinazene among the other vinylic monomers carrying electron withdrawing groups such as acrylonitrile, acrylic esters, or perhaps cyano substituted styrenes. Thus, the vinyl dicyanoimidazoles are a new family of monomers, prepared by a novel synthesis starting from DAMN, and have many useful properties.

The polymerization of the parent monomer, Vinazene, by a thermally induced Michael addition process, gives an imidazole in-chain structure. However, it also polymerizes vinylically by initiation at 110° C. with benzoyl peroxide to give viscous solutions which form free-standing films upon evaporation. This vinylic polymer has several unusual properties.

The Vinazene monomer, like other dicyanoimidazoles, has a 1-H that is quite acidic, pK~5.0, and gives a pattern in its infrared spectrum which is characteristic of strong 1,3 hydrogen bonding. In the vinylic homopolymer, this hydrogen bonding will persist either in intramolecularly along the chain backbone, or intramolecularly, having the effect of locking the chains together.

In the cartoon of FIG. 10, an idealized intramolecular hydrogen bonding pattern is shown for a syndiotactic chain with alternate imidazole rings abbreviated, Im, for clarity. While this orderly array is not possible for an atactic random coil structure, the likelihood of strong intra or intermolecular 1,3 hydrogen bonding is high, since this feature is evident in crystal structures done on small cyanoimidazole molecules. The polymer is, however, readily soluble in base, and one might hope that, by forming a concentrated dope of polymer in base, one could then spin the dope into acid, precipitating polymer fiber.

The 1-H polymer, with its facile reactions at the one nitrogen, can be envisaged as a site for grafting, crosslinking, or as a site for acylation transfer catalysis. In fact, imidazoles are commonly used for this latter purpose, but it would be extremely convenient to have a polymer immobilized version of such a catalyst. Appropriately grafted long chain branches could confer hydrocarbon solubility, improved processability, or opportunities for side chain functionality of almost any type. All that is needed for their synthesis is a suitable electrophilic reagent. Crosslinking reagents of different lengths could establish aspects of chain microstructure and provide for different degrees of stiffness in the products.

Since the alkyl substituted Vinazenes polymerize so readily, an alternative way to prepare the 1-H polymer is by a protection, polymerization, deprotection sequence analogous to the preparation of polyvinyl alcohol. This approach might be useful for preparing copolymers of 1-protected monomer with other monomers. The masked form would be more compatible with styrene or acrylonitrile, for example. After copolymerization, the protecting group could be removed, or modified, to afford the desired functionality, which could be used for crosslinking, or other grafting reactions. This approach to polymer modification has seen application in polybenzimidazoles, but cyanoimidazoles are more facile leaving groups and offer a different range of substitution possibilities. Nitrile functionalities are readily hydrolyzed to carboxylic acids, so another use of this polymer could be as a carboxylic acid cation exchange resin.

As noted above, the Vinazene monomer can be cleanly alkylated in high yield without inducing polymerization. An initial polymerization attempt on this monomer, using AIBN in acetonitrile, led to poly(methyl Vinazene), a hard, pale yellow polymer, in good yield. The structure is readily discerned from the NMR and IR spectra to be a normal polymethylene chain structure. The intrinsic viscosity in DMSO was $[\eta]=0.6$ dL/g, and using styrene values for the Mark Houwink constants, $M_v=140,000$.

Although polymerization of methyl Vinazene can be accomplished using free radical initiation, this monomer also polymerizes by anionic initiation. These experiments take advantage of the electron withdrawing power of the cyanoimidazole ring, and the initiator fluorenyl Li. Fluorene, (pK~25) is among the mildest carbanions used for inducing anionic polymerization and will initiate acrylonitrile, but not styrene. Interestingly, methyl Vinazene is initiated by Li fluorenyl in acetonitrile solution. Optimized conditions for an anionic polymerization could lead to block copolymers with styrene or acrylonitrile. Stereoregular polymerization is also a possibility, since the steric properties of the monomer are similar to styrene, and syndiotactic polystyrene is now known.

Use of the Novel Compounds in Oligomer Synthesis

Figure 26:
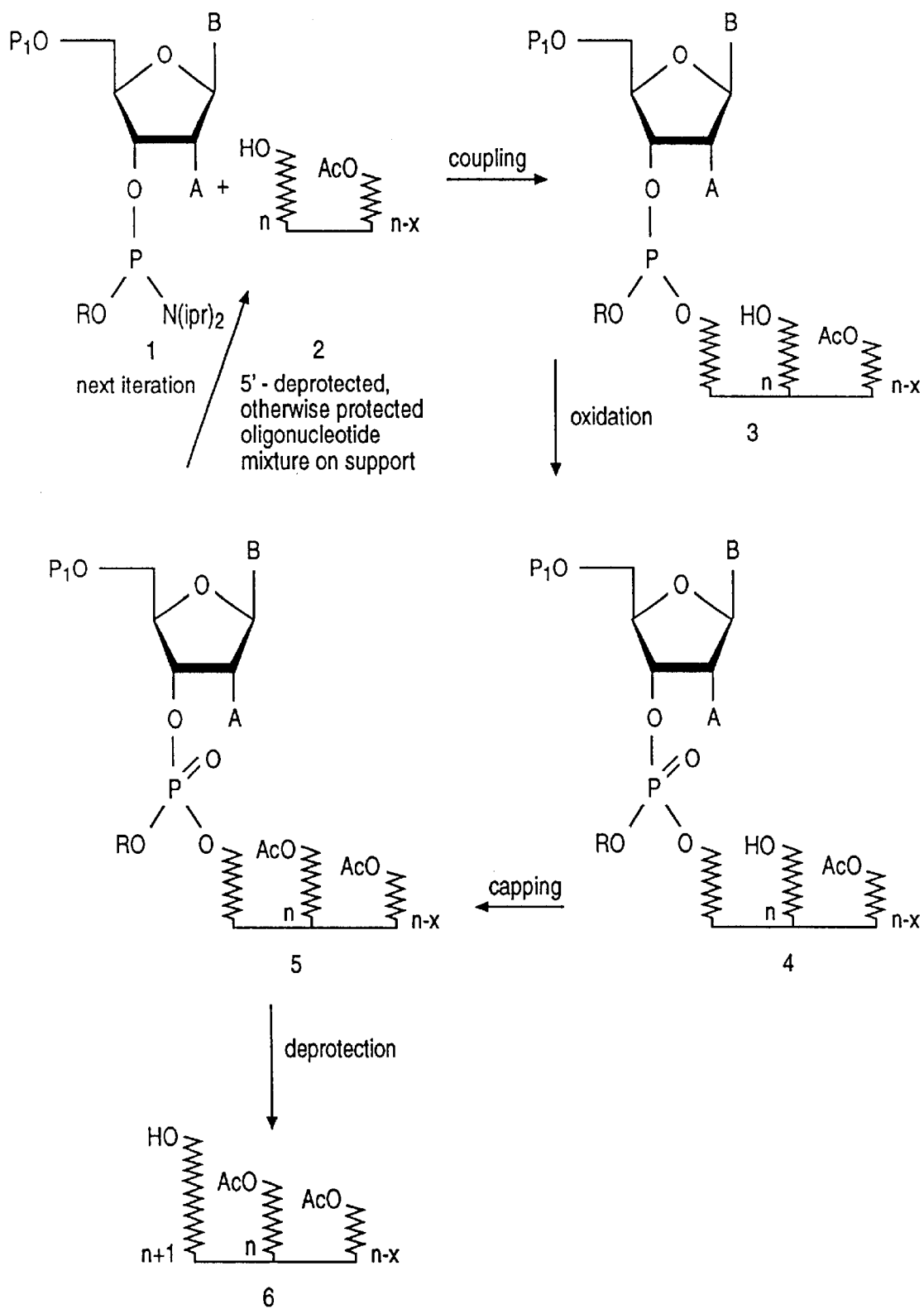
FIG. 26 is a schematic of a reaction sequence for synthesis of oligonucleotides.

The current state of the art in oligonucleotide synthesis is automated solid phase synthesis of oligonucleotides by the phosphoramidite method, which is illustrated in FIG. 26. (Beaucage and Iyer (1992) Tetrahedron 48:2223–2311; Zon and Geiser (1991) Anti-Cancer Drug Design 6:539–568: Matteucci and Caruthers (1981) J. Am. Chem. Soc. 103:3185–3191). General background for this technology using tetrazol condensing agent is also found in articles by M. H. Caruthers, Science, 1985, 281 and J. Chem. Ed., Vol. 66, No. 7, July, 1989, 577. Briefly, the 3'-terminal nucleoside of the oligonucleotide to be synthesized is attached to a solid support and the oligonucleotide is synthesized by addition of one nucleotide at a time while remaining attached to the support. As depicted in FIG. 26, a nucleoside monomer is protected ($P_1$) and the phosphoramidite is prepared (1). The phosphoramidite (referred to as the 5'-protected monomer unit) is then covalently attached to the growing oligonucleotide chain (2), via a phosphite triester linkage, through the 5'-hydroxy group of the ribose ring of the growing oligonucleotide chain to yield the oligonucleotide product (3), in which the majority of the growing oligonucleotide chain has been extended by one nucleotide. The product (3) is then oxidized to yield the phosphate triester (4). Prior to the addition of the next base to the growing nucleotide chain, the 5'-hydroxyl group must be deprotected. As can be seen in FIG. 26 (compound 4), however, not all of the reactive sites on the solid support react with the 5'-protected monomer. These unreacted sites (referred to as failure sequences) must, therefore, be protected (referred to as capping) (5) prior to deprotection of the 5'-hydroxyl group (6). Subsequent monomers, which have also been protected and converted to the phosphoramidite, are then sequentially added by coupling the 5'-end of the growing oligomer to the 3'-end of the monomer. Each coupling reaction extends the oligonucleotide by one monomer via a phosphite triester linkage. When the synthesis is complete, the desired oligonucleotide 6, the n+1 sequence, is deprotected and cleaved from the resin, together with all of the failure sequences (n, n−x).

In the most preferred embodiment of the invention, the monomer unit consists of a 5'-protected phosphoramidite or H-phosphonate, wherein the protecting group is a substituted trityl group, levulinic acid group or silyl ether group. The preferred substitution on the protecting group is a diene functionality, which can react, via a Diels-Alder reaction, with a solid support, such as a resin, membrane or polymer that has been derivatized with a dienophile. In this embodiment, the unreacted oligonucleotide starting material is separated from the reacted nucleotide product based on the selective or specific covalent reaction of the 5'-protecting group with a derivatized resin.

Certain terms used to describe the invention herein are defined as follows:

"Nucleoside" means either a deoxyribonucleoside or a ribonucleoside or any chemical modifications thereof. Modifications of the nucleosides include, but are not limited to, 2'-position sugar modifications, 5-position pyrimidine modifications, 8-position purine modifications, modifications at cytosine exocyclic amines, substitution of 5-bromouracil, and the like.

Figure 27:
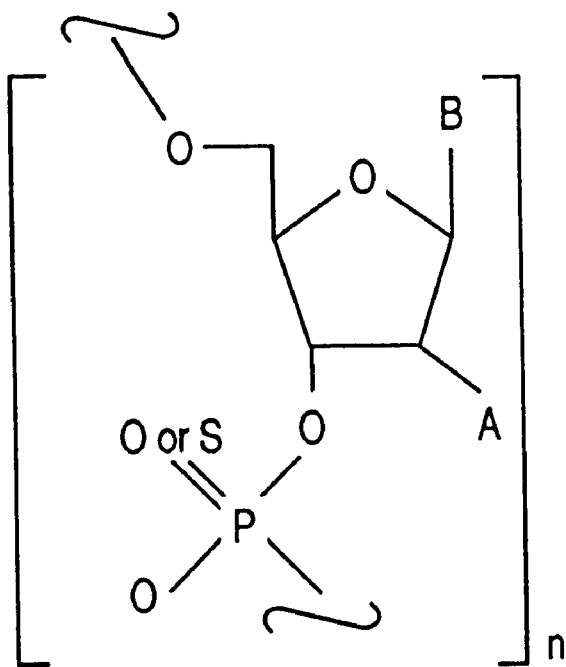
FIG. 27 shows a general structure of a representative oligonucleotide synthesized by a method according to the invention where the coupling agent is the polymer of the invention.

"Oligonucleotide" refers to either DNA or RNA or any chemical modifications thereof. The oligonucleotides synthesized by the method of this invention are depicted generally as in FIG. 27. In one embodiment, n=1 to 1,000, A is a 2'-sugar substituent, B is a nucleobase, and the phosphorous (P) is double bonded to oxygen (O) or sulfur (S).

A "solid support" as used herein refers to a resin, membrane, phase, polymer, polymer precursor, or soluble polymer that can undergo phase transition. A solid support also refers to a resin, membrane, phase, polymer, polymer precursor, or soluble polymer that has been derivatized.

Figure 28:
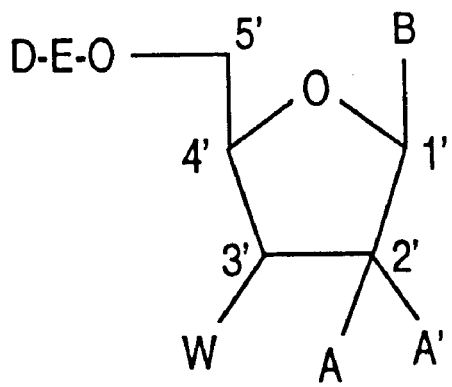
FIG. 28 shows a general structure of a 5'-protected monomer unit which is usable to form a block of oligonucleotides (growing nucleotide chain) prepared by the synthesis methods of the invention.

Another example of "5'-protected monomer unit" is generally as in FIG. 28, including the conventional number for the ribose ring. In FIG. 28, B is a nucleobase; A and A' are 2'-sugar substituents; W is independently selected from the group consisting of a phosphoramidite, H-phosphonate, trialkylphosphat, phosphoramidate, protected oligonucleotide and methyl-phosphonate; and D–E is an alcohol (hydroxyl) protecting group(s) which serves as an anchor for partitioning the successfully reacted oligonucleotide product away from the unreacted oligonucleotide starting material. In a preferred embodiment of the invention: W is a phosphoramidite or H-phosphonate; A and A' are in-dependently selected. (See PCT/US96/16668 (WO 97/14706 published Apr. 24, 1997) taking priority from U.S. Ser. No. 60/005,619 filed Oct. 17, 1996, "Method for Solution Phase Synthesis of Oligonucleotides", and PCT/IB96/01185 (WO 97/14710 published Apr. 24, 1997) taking priority from U.S. Ser. No. 08/546,198 filed Oct. 20, 1995, "Preparation of Phosphorothioate Oligomers", each of which is incorporate herein by reference in its entirety as a background teaching tool).

In another embodiment the 5'-deprotected oligonucleotide is not required to be attached to a support. Instead, a material is used to interact selectively with the 5'-protecting group (D–E) of FIG. 28. For example, the product is captured or retained on a solid resin support by covalent reaction of the 5'-protecting group constituent with the resin. Then, unreacted starting material not carrying the 5'-protecting group is washed away.

"Starting material" as used herein refers to the compound that is reacted with the 5'-protected monomer unit during each cycle of synthesis to produce an oligomer that has been extended by one of more nucleotides. The starting material can be designed to produce a [5',3'] linkage between nucleotides or a [3',3'] linkage between nucleotides, depending on the desired oligonucleotide product. In the first instance, the starting material is a 5'-deprotected otherwise protected oligonucleotide of length n, in the second case the starting material is a 3'-deprotected otherwise protected oligonucleotide of length n, wherein n is an integer from 1–1000. The starting material is 2',3'-protected by protecting groups, such as base labile groups, that are compatible with the reaction of the 5'-protected monomer units with the starting material and with 5'-deprotection reactions. Additionally, because the process consists of the controlled and sequential polymerization of an oligonucleotide, the starting material of one cycle is typically the deprotected product from the previous cycle. Because in one embodiment, the process does not require that the 3'-terminal nucleotide be anchored to a solid support, the starting material can include non-nucleoside modifications. Non-nucleoside modifications can be introduced to the 3'-terminus which would not ordinarily be possible by solid phase synthesis. Non-nucleoside modifications to the 3'-terminus of the starting material include, but are not limited to, the use of polyethylene glycol monomethylether (molecular weight 5,000 to 100,000) (PEG) or other high molecular weight non-immunogenic units as the 3'-terminal monomer for preparation of oligonucleotides with improved pharmacokinetic properties.

"Product" as used herein refers to an oligonucleotide that is produced by the covalent reaction of the 5'-protected monomer unit with the starting material during each cycle. As stated above, if the starting material is a 5'-deprotected oligonucleotide of length n and the 5'-monomer unit is a single nucleotide, the product of the reaction will be a 5'-protected oligonucleotide of length n+1. If the 5'-protected monomer unit is an oligonucleotide block of length m, the product of the reaction will be a 5-protected oligonucleotide of length n+m. The product from a particular cycle is then 5'-deprotected and becomes the starting material for the next cycle.

A "failure sequence" refers to the starting material from a particular cycle that fails to react with the 5'-protected monomer unit during that cycle.

The growing oligonucleotide chain or block refers to either a 5'-deprotected oligonucleotide chain or a 5'-protected oligonucleotide chain that has been prepared by the sequential addition of nucleotides (N) beginning with the 3'-terminal nucleotide of the desired nucleotide using the method of this invention. After each reaction cycle of the process, the growing oligonucleotide increases in length by at least one oligonucleotide, and becomes the starting material for the next reaction cycle. As used herein, the term can refer to either starting material or product, and one of ordinary skill in the art will recognize what is intended by the term in a particular context.

In a representative synthesis method, a 5'-protected monomer unit, such as phosphoramidite, is added to a starting material in solution, in the presence of an activator, to yield a product to which one nucleotide has been added via a phosphite triester linkage. In a preferred embodiment, the activator is a polymer according to the invention. The starting material is a 5'-deprotected otherwise protected oligonucleotide of length n, wherein n is an integer between 1 and 1000, and the product is a 5'-protected oligonucleotide of length n+1. The 5'-deprotected oligonucleotide starting material need not be anchored to a solid support, but rather, using standard methods, is simply 2', 3'-protected by protecting groups, such as base labile groups, that are compatible with the reaction of the 5'-protected monomer units with the starting material and with 5'-deprotection reactions. Thus, modifications can be introduced to the 3'-terminus which are not possible by solid phase synthesis. This includes, but it not limited to, the use of polyethylene glycol mono-methylether (molecular weight 5,000 to 100,000) or other high molecular weight non-immunogenic units.

After completion of the reaction between the 5'-protected monomer unit and starting material, the reaction mixture contains three species: unreacted 5'-protected monomer unit, unreacted starting material, and the product of the reaction, compound, which is a 5'-protected olionucleotide of length n+1. As discussed above, any of the starting material (a 5'-deprotected oligonucleotide of length n) which fails to react with the 5'-protected monomer unit, is referred to as the failure sequence, as this sequence was not extended. The product of the reaction, compound, is a 5'-protected oligonucleotide chain extended by one nucleotide (length n+1), by the covalent reaction of the 5'-hydroxy group of starting material, an oligonucleotide of length n with the 3'-phosphoramidite group of the 5'-protected monomer unit. The product, compound, is the major component, and the 5'-protected monomer unit and the starting material that did not react are present only in minor amounts.

At this stage of the process, it is necessary to remove the unreacted 5'-protected monomer unit from the reaction mixture, both to purify the materials, and to recover the monomer starting material. According to this embodiment, non-reacted monomer is reacted to form an easily removable ionic species. Oxidation of the phosphite triester to phosphate triester may be carried out in the same reaction flask simply by addition of an oxidizing agent. In situ oxidation gives the desired oligonucleotide product, the phosphate salt of monomer, as well as unreacted oligonucleotide starting material. The monomer phosphate salt is the only free salt in the reaction mixture and thus is easily removed by techniques known to those in the art, including but not limited to, filtration through an anion exchange resin or membrane or extraction with an aqueous phase. In an alternate variation of this embodiment of the invention, the 3'-terminal monomer is a polyethylene glycol mono-methylether of molecular weight 5,000 to 100,000, preferably 20,000. In this case, a simply molecular weight cut-off membrane can be used to remove monomer. After the unreacted monomer has been removed from the reaction mixture, the remaining filtrate may then be partitioned in any manner suitable to separate the "oligonucleotide product" from the "failure sequence."

Example of Oligomer Synthesis

This example shows the utility of polymers derived from 1-H-2-vinyl-4,5-dicyanoimidazole in promoting the phosphoramidite coupling reaction used in the laboratory synthesis of oligomers. The method of synthesis using the new activating agent of the invention will be exemplified by synthesis of DNA.

Figure 29:
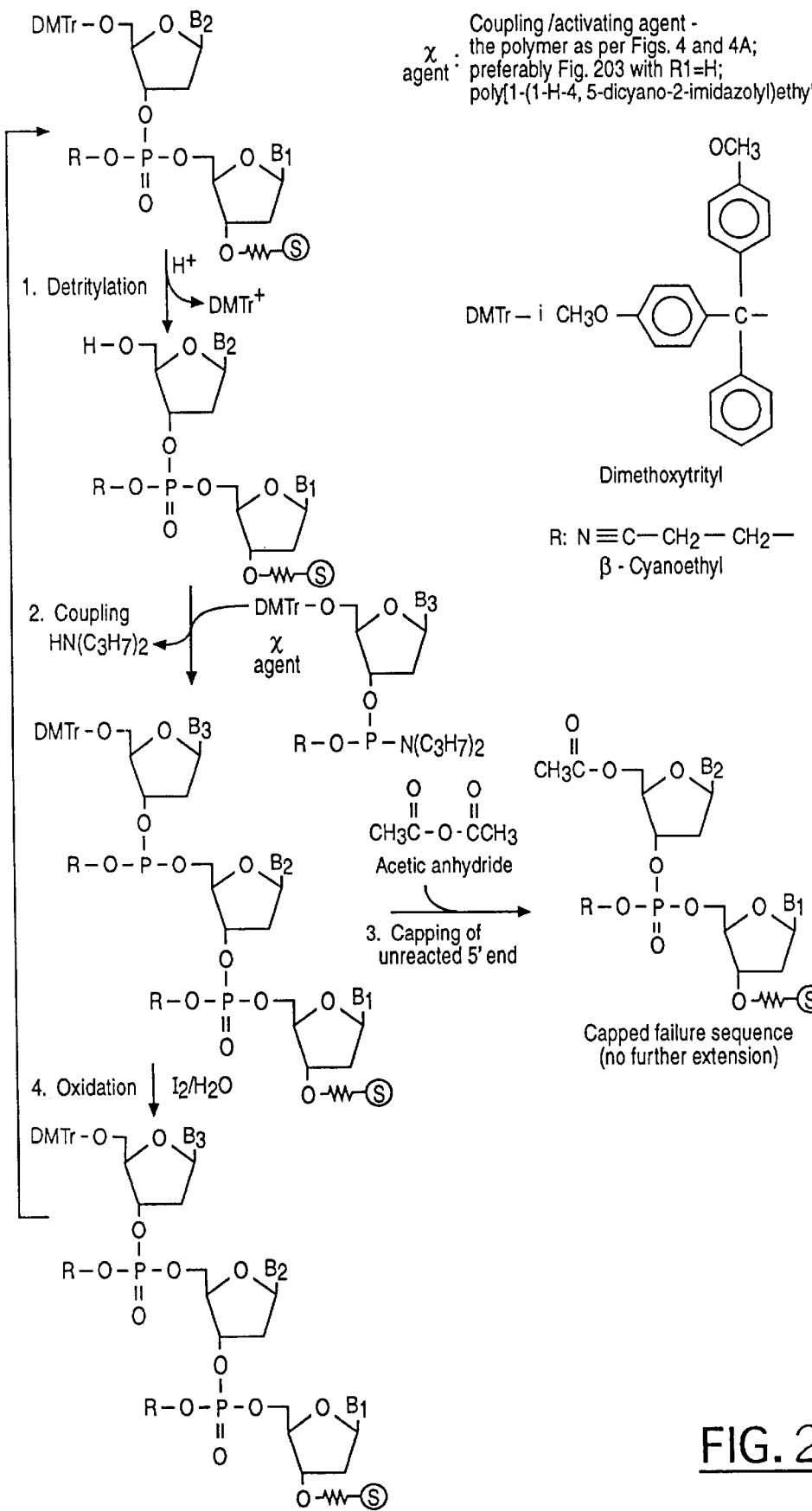
FIG. 29 shows a reaction sequence for synthesis of oligomers by the steps of detritylation; coupling; capping of unreacted material; and oxidation of coupled material. The coupling/activating agent ($\psi$) of the invention is shown with reference to FIGS. 4, 4A and 10.

The chemical synthesis of DNA which proceeds by cycles of addition of deoxymononucleotide, is shown in FIG. 29. FIG. 29 shows a reaction sequence for synthesis of oligomers by the steps of detritylation; coupling; capping of unreacted material; and oxidation of coupled material. The coupling/activating agent ($\chi$) of the invention is shown with reference to FIGS. 4, 4A and 10. In this embodiment, a support is used, but is optional per embodiments described above. In step 1, detritylation of a support bound and protected nucleotide occurs, typically, by treatment with dichloroacetic acid in an inert solvent such as methylene chloride. The deprotected nucleotide is carefully washed and dried with acetonitrile.

In step 2, the deprotected nucleotide reacts with a protected doxynucleoside 3'-phosphoramidite. The synthesis proceeds in the presence of the preferred polymer activator with preferably R1=H (FIG. 10). This polymer is poly[1-(1H-4,5-dicyano-2-imidazolyl) ethylene]. The polymer is added as a solid or on a support such as silica. The polymer condenses with the free 5'-hydroxyl, and then promotes the reaction of the phosphoramidate to effect coupling with the loss of isopropylamine. This salt is usually washed away in conventional methods absent the polymer activator of the invention. In the case of the polymer promoter/activator, a polymeric salt is formed. The polymeric salt can be removed by filtration and regenerated by treatment with strong acid, and used again.

Steps 3 and 4, the final two steps in the synthesis cycle, are capping and oxidation. The capping reaction, step 3, is carried out with acetic anhydride and dimethylaminopyridine, and its purpose is to acylate any DNA segments that fail to react during coupling. These unreacted oligomers, if not capped, might get involved in subsequent steps where their removal would be more difficult to achieve. The oxidation step uses $I_2$ in 2,6-lutidine/water/tetrahydrofuran (2:2:1 v/v/v) to convert the phosphite triester to the phosphate triester. After the sequential addition of nucleotides is completed, the DNA is freed of any remaining protecting groups, the beta-cyanoethyl protecting group on the phosphorous atoms is removed, and the ester linkage connecting the DNA to the support is hydrolyzed.

Note that the beta-cyanoethyl protecting group is a chiral auxiliary which has left- and right-handed features to aid in alignment of units to enhance chain formation. Such chiral auxiliary groups are known in the art for being hand-like mirror images that are not superimposable.

While this invention has been described in terms of certain embodiments thereof, it is not intended that it be limited to the above description, but rather only to the extent set forth in the following claims.

The embodiments of the invention in which an exclusive property or privilege is claimed are defined in the following claims:

What is claimed is:

1. In a method for the synthesis of oligonucleotides comprising the steps of:

a) reacting a 5'-protected monomer unit with an oligonucleotide unit in the presence of a coupling agent to form a reaction mixture containing a product, said product of said reaction being a 5'-protected oligonucleotide having its length increased by joining said monomer unit to said oligonucleotide unit; and b) separating the product from the unreacted starting material, unreacted 5'-protected monomer unit, side products, and reagent; the improvement comprising:

said coupling agent being a polymer consisting of cyclic imidazole units having nitrogen at the 1 and 3 positions; a carbon at each of the 2, 4 and 5 positions; and radical substituents G1 and G2 carried at respective said 4 and 5 positions, where G1 and G2 are each independently selected from a group of electron-withdrawing substituents; wherein each of said imidazole units is connected to the main polymer chain through said 2 position; providing a polymer of the formula:

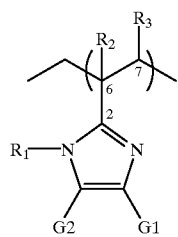

where R1 is hydrogen or a substituted or unsubstituted alkyl having up to 10 carbon atoms, R2 is hydrogen or a substituted or unsubstituted alkyl having up to 4 carbon atoms, and R3 is hydrogen.

2. The method according to claim 1 wherein R1 is hydrogen, and G1 and G2 are each cyano, and said polymer has the formula:

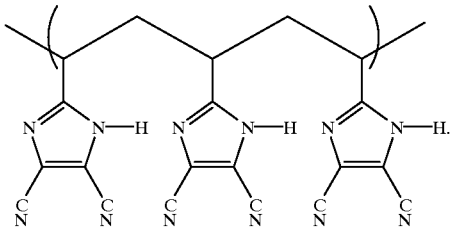

3. The method according to claim 1 wherein said G1 and G2 are each independently selected from the group consisting of cyano, carboxy amide, carboxylic acids and carboxylic acid esters.

4. The method according to claim 1 where G1 and G2 are each independently selected from the group consisting of cyano, and substituents derived from cyano.

5. The method according to claim 1 wherein the 5'-protected monomer unit is a single nucleotide (N), the oligonucleotide unit is a block of multiple units (N>1), and the product is a 5'-protected oligonucleotide having a length of N+1.

6. The method according to claim 1 wherein the 5'-protected monomer unit is an oligonucleotide of block length M, the oligonucleotide unit is an oligonucleotide of block length N, and the product of reaction is a 5'-protected oligonucleotide of length N+M.

7. The method according to claim 1 wherein the 5'-protected monomer unit has the following formula:

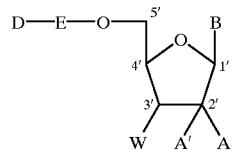

wherein B is a nucleobase; A and A' are 2'-sugar substituents; W is independently selected from the group consisting of a phosphoramidite, a H-phosphonate, a trialkylphosphate, a methyl phosphonate, a phosphoramidate and a protected oligonucleotide, wherein said protected oligonucleotide has a 3'-terminal group selected from the group consisting of a phosphoramidite, a H-phosphonate, a phosphotriester, a methyl phosphonate, phosphoramidate; and D–E is an alcohol protecting group(s).

8. In a method for the nthesis of oligonucleotides by reacting deprotected nucleotide with a protected deoxynucleoside 3'-phosphoramidite in the presence of an coupling agent, the improvement comprising: said coupling agent being a polymer having the formula:

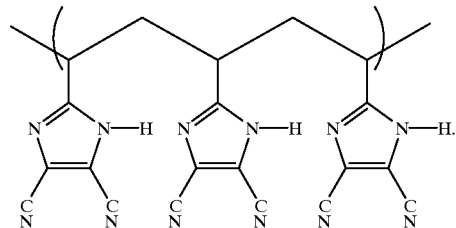

9. The method according to claim 8 wherein the deprotected nucleotide has the formula

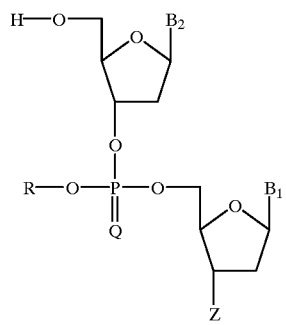

where R is a chiral auxiliary protecting group; Z is a hydroxyl-protecting group, a link to a solid support, or a non-immunogenic group; Q is oxygen or sulphur; and B1 and B2 each represent a nucleobase.

10. The method according to claim 8 wherein the protected deoxynucleoside 3'-phosphoramidite has the formula

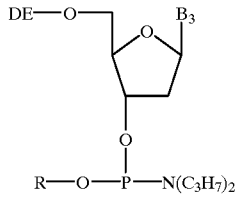

where R is a chiral auxiliary protecting group; B3 represents a nucleobase; and DE is a hydroxyl-protecting group.

* * * * *